US012364661B2

(12) United States Patent
John et al.

(10) Patent No.: US 12,364,661 B2
(45) Date of Patent: Jul. 22, 2025

(54) DEFORMABLE NANO-SCALE VEHICLES (DNVS) FOR TRANS-BLOOD BRAIN BARRIER, TRANS-MUCOSAL, AND TRANSDERMAL DRUG DELIVERY

(71) Applicant: The Regents of the University of California, Oakland, CA (US)

(72) Inventors: Varghese John, Los Angeles, CA (US); Ichiro Nishimura, Venice, CA (US); Naren Subbiah, Danville, CA (US); Jesus Campagna, Playa Del Rey, CA (US); Patricia R. Spilman, Mill Valley, CA (US); Mohammad Parvez Alam, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/774,575

(22) PCT Filed: Nov. 17, 2016

(86) PCT No.: PCT/US2016/062552
§ 371 (c)(1),
(2) Date: May 8, 2018

(87) PCT Pub. No.: WO2017/087685
PCT Pub. Date: May 26, 2017

(65) Prior Publication Data
US 2018/0318216 A1   Nov. 8, 2018

Related U.S. Application Data

(60) Provisional application No. 62/258,217, filed on Nov. 20, 2015.

(51) Int. Cl.
*A61K 9/127*   (2025.01)
*A61K 9/00*   (2006.01)
(Continued)

(52) U.S. Cl.
CPC ............ *A61K 9/127* (2013.01); *A61K 9/0014* (2013.01); *A61K 9/006* (2013.01); *A61K 9/0087* (2013.01);
(Continued)

(58) Field of Classification Search
CPC .. A61K 9/127; A61K 47/6911; A61K 9/1272; A61K 9/0087; A61K 9/107;
(Continued)

(56) References Cited

U.S. PATENT DOCUMENTS 4,704,355 A   11/1987   Bernstein
5,686,082 A   11/1997   N'Guyen
(Continued)

FOREIGN PATENT DOCUMENTS

BR   PI1104941 A2   7/2013
CN   1613504 A   5/2005
(Continued)

OTHER PUBLICATIONS

Jahn, A., et al in American Chemical Society, vol. 4, No. 4, pp. 2077-2087, 2010.*
(Continued)

*Primary Examiner* — Isaac Shomer
(74) *Attorney, Agent, or Firm* — Foley Hoag LLP; David P. Halstead; David Surry

(57) ABSTRACT

In various embodiments deformable nano-scale vehicles (DNV) are provided that are useful for the delivery of therapeutic agents. In certain embodiments the DNVs are capable of transdermal delivery and can additionally cross the blood-brain barrier.

17 Claims, 17 Drawing Sheets

(51) Int. Cl.

| | | |
|---|---|---|
| A61K 9/107 | (2006.01) | |
| A61K 9/1272 | (2025.01) | |
| A61K 31/428 | (2006.01) | |
| A61K 38/17 | (2006.01) | |
| A61K 38/50 | (2006.01) | |
| A61K 47/64 | (2017.01) | |
| A61K 47/69 | (2017.01) | |
| A61P 25/14 | (2006.01) | |
| A61P 25/16 | (2006.01) | |
| A61P 25/28 | (2006.01) | |
| A61P 35/00 | (2006.01) | |
| C12N 15/113 | (2010.01) | |
| A61K 9/19 | (2006.01) | |
| A61K 9/70 | (2006.01) | |

(52) U.S. Cl.
CPC ............ *A61K 9/107* (2013.01); *A61K 9/1272* (2013.01); *A61K 31/428* (2013.01); *A61K 38/1709* (2013.01); *A61K 38/50* (2013.01); *A61K 47/644* (2017.08); *A61K 47/6911* (2017.08); *A61P 25/14* (2018.01); *A61P 25/16* (2018.01); *A61P 25/28* (2018.01); *A61P 35/00* (2018.01); *C12N 15/113* (2013.01); *C12Y 305/01* (2013.01); *A61K 9/0019* (2013.01); *A61K 9/0085* (2013.01); *A61K 9/19* (2013.01); *A61K 9/70* (2013.01); *C12N 2310/141* (2013.01)

(58) Field of Classification Search
CPC .. A61K 31/428; A61K 38/1709; A61K 38/50; A61K 47/644; A61K 9/0014; A61K 9/006; A61K 9/0019; A61K 9/70; A61K 9/19; A61K 9/0085; A61P 25/14; A61P 25/28; A61P 25/16; A61P 35/00; C12N 15/113; C12N 2310/141; C12Y 305/01
See application file for complete search history.

(56) References Cited

U.S. PATENT DOCUMENTS

| | | | |
|---|---|---|---|
| 5,858,398 A | 1/1999 | Cho et al. | |
| 7,829,113 B2* | 11/2010 | Okada | A61K 9/1271 424/450 |
| 7,927,622 B1* | 4/2011 | Cevc | A61K 9/0043 424/450 |
| 2002/0048596 A1* | 4/2002 | Cevc | A61K 9/127 424/450 |
| 2004/0219202 A1* | 11/2004 | Fletcher | A61K 9/1273 424/450 |
| 2006/0276393 A1 | 12/2006 | Milburn et al. | |
| 2008/0311184 A1* | 12/2008 | Cevc | A61K 9/127 424/450 |
| 2009/0004275 A1* | 1/2009 | Martyn | A61K 38/28 514/1.1 |
| 2009/0017108 A1* | 1/2009 | Yuzhakov | A61K 31/7056 424/450 |
| 2009/0082400 A1 | 3/2009 | Lee et al. | |
| 2011/0178456 A1* | 7/2011 | Aguilar-Mendoza | A61M 35/00 604/20 |
| 2012/0014936 A1 | 1/2012 | Natoli et al. | |
| 2012/0195947 A1 | 8/2012 | Perumal et al. | |
| 2013/0115273 A1 | 5/2013 | Yang et al. | |
| 2013/0259922 A1* | 10/2013 | Haas | A61K 9/1272 424/450 |
| 2014/0017302 A1 | 1/2014 | Cevc | |
| 2014/0086979 A1 | 3/2014 | De Rosa et al. | |
| 2014/0147390 A1 | 5/2014 | Exner et al. | |
| 2015/0110855 A1* | 4/2015 | Cipolla | A61K 9/0078 424/450 |
| 2015/0209282 A1 | 7/2015 | Chu et al. | |
| 2015/0216899 A1 | 8/2015 | Pusic et al. | |
| 2015/0320706 A1 | 11/2015 | Imbimbo et al. | |
| 2016/0243192 A1 | 8/2016 | Seeger et al. | |
| 2018/0028600 A1 | 2/2018 | Hong et al. | |
| 2018/0067121 A1 | 3/2018 | Naasani | |
| 2018/0170969 A1 | 6/2018 | Bond et al. | |
| 2018/0185285 A1 | 7/2018 | Gupta et al. | |
| 2018/0305412 A1 | 10/2018 | Bond et al. | |
| 2018/0369410 A1 | 12/2018 | Hong et al. | |
| 2019/0015331 A1 | 1/2019 | Elliman et al. | |
| 2019/0049438 A1 | 2/2019 | Liu et al. | |
| 2019/0093105 A1 | 3/2019 | Gibbings et al. | |
| 2019/0112351 A1 | 4/2019 | Ishii et al. | |
| 2019/0135873 A1 | 5/2019 | Bond et al. | |
| 2019/0151456 A1 | 5/2019 | McConnell et al. | |
| 2019/0160097 A1 | 5/2019 | Pusic et al. | |
| 2019/0231694 A1 | 8/2019 | Lim | |
| 2019/0343767 A1 | 11/2019 | Haraszti et al. | |
| 2019/0365653 A1 | 12/2019 | Hong et al. | |
| 2020/0030457 A1 | 1/2020 | John et al. | |
| 2020/0046647 A1 | 2/2020 | Yuk | |
| 2023/0285291 A1 | 9/2023 | Campagna et al. | |

FOREIGN PATENT DOCUMENTS

| | | | | |
|---|---|---|---|---|
| CN | 1951368 | A | | 4/2007 |
| CN | 103446055 | A | | 12/2013 |
| CN | 105287382 | A | | 2/2016 |
| CN | 106389137 | A | | 2/2017 |
| EP | 0450991 | | * | 2/1991 |
| EP | 2431023 | A1 | | 3/2012 |
| JP | 2005213261 | A | | 8/2005 |
| JP | 2014198720 | A | | 10/2014 |
| WO | WO 91/04014 | A1 | | 4/1991 |
| WO | WO-2010083778 | A1 | | 7/2010 |
| WO | WO-2010095940 | A2 | | 8/2010 |
| WO | WO 2010/104865 | A2 | | 9/2010 |
| WO | WO 2010/149785 | A1 | | 12/2010 |
| WO | WO-2013059617 | A1 | * | 4/2013 ............ A61K 38/08 |
| WO | WO-2014015027 | A1 | * | 1/2014 ............ A61K 38/07 |
| WO | WO 2017/087685 | A1 | | 5/2017 |
| WO | WO 2018/187240 | A1 | | 10/2018 |
| WO | WO 2019/094679 | A1 | | 5/2019 |
| WO | WO-2019203706 | A1 | | 10/2019 |
| WO | WO-2021/207273 | A1 | | 10/2021 |

OTHER PUBLICATIONS

Yang, T., et al in Chem. Pharm. Bull. vol. 50, # 6, pp. 749-753, 2002.*
Yaw-Bin Huang, Ming-Jun Tsai, Pao-Chu Wu, Yi-Hung Tsai, Yi-Hsin Wu, and Jia-You Fang. "Elastic liposomes as carriers for oral delivery and the brain distribution of (+)-catechin." Journal of Drug Targeting, vol. 19(8), 2011, pp. 709-718. (Year: 2011).*
Oluwatosin A. Ogunsola, Margaret E. Kraeling, Sheng Zhong, Darrin J. Pochan, Robert L. Bronaugh and Srinivasa R. Raghavan. " Structural analysis of "flexible" liposome formulations: new insights into the skin-penetrating ability of soft nanostructures." Soft Matter, vol. 8, 2012, 10226-10232. (Year: 2012).*
PCT International Search Report and Written Opinion dated Feb. 16, 2017 issued in PCT/US2016/062552.
PCT International Preliminary Report on Patentability and Written Opinion dated May 22, 2018 issued in PCT/US2016/062552.
PCT International Search Report and Written Opinion dated Aug. 29, 2018 issued in PCT/US2018/025749.
PCT International Search Report and Written Opinion dated Feb. 28, 2019 issued in PCT/US2018/059960.
EP Extended Search Report dated May 28, 2019 issued in EP 16867146.9.
Burnes, (2012) "Quantifying biomass changes of single cells during antigen specific CD8+ T cell mediated cytotoxicity [electronic resource] / by Daina Laura Burnes.", *UCLA Library Catalog* 1 page; Retrieved on Nov. 8, 2017 from UCLA Library Catalog Holdings Information.

(56) References Cited

OTHER PUBLICATIONS

El Maghraby et al., (1999) "Skin delivery of oestradiol from deformable and traditional liposomes: mechanistic studies." *Journal of Pharmacy and Pharmacology*, 51: 1123-1134.
Fleisher et al., (1995) "Topical Delivery of Growth Hormone Releasing Peptide Using Liposomal Systems: An in Vitro Study Using Hairless Mouse Skin." *Life Sci.* 57(13): 1293-7.
Ghanbarzadeh, S. et al., (2013) "Enhanced transdermal delivery of diclofenac sodium via conventional liposomes, ethosomes, and transfersomes." *BioMed Research International*, vol. 2013, Article ID 616810, 7 pages, http://dx.doi.org/10.1155/2013/616810.
Goindi, S. et al., (2013) "Development of novel elastic vesicle-based topical formulation of cetirizine dihydrochloride for treatment of atopic dermatitis." *AAPS PharmSciTech*, 14(4): 1284-1293.
Hasan et al., (2013) "Formulation and evaluation of metformin hydrochloride-loaded niosomes as controlled release drug delivery system", *Drug Delivery*, 20(3-4): 120-126.
Holpuch et al., (2010) "Nanoparticles for Local Drug Delivery to the Oral Mucosa: Proof of Principle Studies." *Pharm Res Pharmaceutical Research* 27(7): 1224-1236.
Huang et al., (2011) "Elastic liposomes as carriers for oral delivery and the brain distribution of (+)-catechin." *Journal of Drug Targeting*, 19(8): 709-718.
Idiart et al., (2004) "Rupture of a Liposomal Vesicle." *Physical Review E* 69(6 Pt 1): 061922 (8 pages).
Jahn et al., (2010) "Microfluidic Mixing and the Formation of Nanoscale Lipid Vesicles", *ACS Nano* 4(4): 2077-2087.
Madhav et al., (2012) "Recent Trends in Oral Transmucosal Drug Delivery Systems: An Emphasis on the Soft Palatal Route." *Expert Opinion on Drug Delivery* 9(6):629-647.
Obregon et al., (2012) "Soluble amyloid precursor protein-alpha modulates beta-secretase activity and amyloid-beta generation" *Nat Commun.*, 3: 777 (9 pages).
Patel et al., (2011) "Advances in Oral Transmucosal Drug Delivery." *Journal of Controlled Release* 153(2): 106-116.
Petelin et al., (1998) "EPR Study of Mucoadhesive Ointments for Delivery of Liposomes into the Oral Mucosa." *International Journal of Pharmaceutics* 173(1-2): 193-202.
Prausnitz et al., (2008) "Transdermal Drug Delivery." *Nat Biotechnol Nature Biotechnology* 26.11 1261-268; [NIH Public Access—Author Manuscript—18 pages].
Salem et al., (2015) "Targeting brain cells with glutathione-modulated nanoliposomes: in vitro and in vivo study", *Drug Design, Development and Therapy*, 9: 3705-3727.
Šentjurc et al., (1999) "Liposomes as a Topical Delivery System: The Role of Size on Transport Studied by the EPR Imaging Method." *Journal of Controlled Release* 59(1): 87-97.
Shmeeda et al., (2010) "Delivery of zoledronic acid encapsulated in folate-targeted liposome results in potent in vitro cytotoxic activity on tumor cells", *Journal of Controlled Release*, 146(1): 76-83.
Singh et al., (2009) "Elastic Liposomal Formulation for Sustained Delivery of Colchicine: In Vitro Characterization and In Vivo Evaluation of Anti-gout Activity." *The AAPS Journal* 11(1): 54-64.
Zhang et al., (2017) "Nanocapsules of therapeutic proteins with enhanced stability and long blood circulation for hyperuricemia management", *Journal of Controlled Release* 255: 54-61.
PCT International Preliminary Report on Patentability and Written Opinion dated Oct. 8, 2019 issued in PCT/US2018/025749.
Ghai et al., (2012) "A Review of Transdermal Drug Delivery Using Nano-Vesicular Carriers: Transfersomes." *Recent Patents on Nanomedicine* 2: 164- 171.
Rai et al., (2017) "Transfersomes as versatile and flexible nanovesicular carriers in skin cancer therapy: the state of the art." *Nano Reviews & Experiments*, [18 pages] https://doi.org/10.1080/20022727.2017.1325708.
Sudhakar et al., (2016) "A Comparison Study of Liposomes, Transfersomes And Ethosomes Bearing Lamivudine." *IJPSR* 7(10): 4214-4221.
PCT International Preliminary Report on Patentability and Written Opinion dated May 12, 2020 issued in PCT/US2018/059960.

EP Extended Search Report dated Nov. 17, 2020 issued in EP 18781490.0.
US Office Action dated Apr. 30, 2020 issued in U.S. Appl. No. 16/498,301.
US Final Office Action dated Nov. 24, 2020 issued in U.S. Appl. No. 16/498,301.
Desmet et al., (2016) "An elastic liposomal formulation for RNAi-based topical treatment of skin disorders: Proof-of-concept in the treatment of psoriasis." *International Journal of Pharmaceutics*, 500: 268-274.
Gupta et al., (2012) "Transfersomes: A Novel Vesicular Carrier for Enhanced Transdermal Delivery of Sertraline: Development, Characterization, and Performance Evaluation." *Sci. Pharm.*, 80: 1061-1080.
Scognamiglio et al., (2013) "Nanocarriers for topical administration of resveratrol: A comparative study." *International Journal of Pharmaceutics* 440(2): 179-187.
Subbiah et al., (2017) "Deformable Nanovesicles Synthesized through an Adaptable Microfluidic Platform for Enhanced Localized Transdermal Drug Delivery." *Journal of Drug Delivery*, 12 pages, DOI: 10.1155/2017/4759839.
Boakye, Cedar H.A., et al., "Ultra-flexible Nanocarriers for Enhanced Topical Delivery of a Highly Lipophilic Antioxidative Molecule for Skin Cancer Chemoprevention", Colloids and Surfaces B: Biointerfaces, 2016, vol. 143, pp. 156-167.
CN Office Action dated Aug. 31, 2021, in application No. CN201880034534.
Elhissi, A. et al., "Nebulization of Ultradeformable Liposomes: The Influence of Aerosolization Mechanism and Formulation Excipients", International Journal of Pharmaceutics, 2012, vol. 436, pp. 519-526.
JP Office Action dated Jan. 17, 2022, in Application No. JP2020-502542 with English translation.
Shao, Kun et al., (2011) "Brain-targeted Drug Nano-delivery System", Journal of Southeast University (Medical Edition) 30(1): 169-184.
JP Office Action dated Nov. 14, 2022, in Application No. JP2020-502542 with English translation.
U.S. Final Office Action dated Oct. 11, 2022, in U.S. Appl. No. 16/498,301.
U.S. Office action dated Feb. 17, 2022, in U.S. Appl. No. 16/498,301.
El-Amouri, S.S. et al., "Normalization and improvement of CNS deficits in mice with Hurler syndrome after long-term peripheral delivery of BBB-targeted iduronidase", Molecular Therapy, Sep. 9, 2014, vol. 22, No. 12, pp. 2028-2037.
EP Office Action dated Dec. 7, 2022 in Application No. EP16867146.9.
Garcia-Manrique, P., et al., "Fully Artificial Exosomes: Towards New Theranostic Biomaterials," Trends in biotechnology, Jan. 2018, vol. 36(1), pp. 10-14.
International Search Report and Written Opinion dated Sep. 23, 2021 in PCT Application No. PCT/US2021/026049.
International Preliminary Report on Patentability and written opinion dated Oct. 20, 2022 in Application PCT/US2021/026049.
International Search Report and Written Opinion dated Jan. 5, 2023 in PCT Application No. PCT/US2022/043243.
Jang, S.C., et al., "Bioinspired Exosome-mimetic Nanovesicles for Targeted Delivery of Chemotherapeutics to Malignant Tumors," ACS nano, Sep. 2013, vol. 7(9), pp. 7698-7710.
Jo, W., et al., "Microfluidic Fabrication of Cell-derived Nanovesicles as Endogenous RNA Carriers," Lab on a chip, Apr. 2014, vol. 14(7), pp. 1261-1269.
Koblan, L.W. et al., "Improving Cytidine and Adenine Base Editors by Expression Optimization and Ancestral Reconstruction", Nature Biotechnology, May 29, 2018, vol. 36, No. 9, pp. 843-846.
Li, SP., et al., "Exosomal Cargo-loading and Synthetic Exosome-mimics as Potential Therapeutic Tools," Acta pharmacologica Sinica, Apr. 28, vol. 39(4), vol. 542-551.
Lin Y T et al., APOE4 Causes Widespread Molecular and Cellular Alterations Associated with Alzheimer's Disease Phenotypes in Human iPSC-Derived Brain Cell Types, Neuron, 2018, vol. 98, pp. 1141-1154.

(56) References Cited

OTHER PUBLICATIONS

PILCH and MUSIAL, "Liposomes with an Ethanol Fraction as an Application for Drug Delivery," Int J Mol Sci. Nov. 29, 2018;19(12):3806 (13 pages). doi: 10.3390/ijms19123806.
Thuronyi, B.W. et al., "Continuous Evolution of Base Editors With Expanded Target Compatibility and Improved Activity", Nature Biotechnology, Sep. 2019, vol. 37, No. 9, pp. 1070-1079.
U.S. Appl. No. 17/917,233, inventors Campagna et al., filed on Oct. 5, 2022.
Final Office Action for U.S. Appl. No. 15/774,575 dated Apr. 7, 2021.
Final Office Action for U.S. Appl. No. 15/774,575 dated Mar. 8, 2023.
Final Office Action for U.S. Appl. No. 15/774,575 dated Oct. 22, 2019.
Non-Final Office Action for U.S. Appl. No. 15/774,575 dated Aug. 24, 2020.
Non-Final Office Action for U.S. Appl. No. 15/774,575 dated Jun. 20, 2022.
Non-Final Office Action for U.S. Appl. No. 15/774,575 dated Mar. 29, 2019.
Non-Final Office Action for U.S. Appl. No. 15/774,575 dated Oct. 27, 2023.
Chen et al., "Transferrin-modified liposome promotes a-mangostin to penetrate the blood-brain barrier," Nanomedicine: Nanotechnology, Biology, and Medicine 12 (2016): 421-430.
Guo et al., "Galangin, a flavonol derived from Rhizoma Alpiniae Officinarum, inhibits acetylcholinesterase activity in vitro," Chemico-Biological Interactions 187 (2010): 246-248.
Ogunsola et al., "Structural analysis of "flexible" liposome formulations: new insights into the skin-penetrating ability of soft nanostructures," Soft Matter 8 (2012): 10226-10232.
Souto et al., "Elastic and ultradeformable liposomes for transdermal delivery of active pharmaceutical ingredients (APIs)." International Journal of Molecular Sciences 22.18 (2021): 9743.
Verma et al., "Therapeutic and cosmeceutical potential of ethosomes: An overview." Journal of advanced pharmaceutical technology & research 1.3 (2010): 274-282.

\* cited by examiner

Liposome loaded with AF-ZOL

DNV loaded with AF-ZOL

Lyophilized AF-ZOL DNV re-suspended after weeks of storage

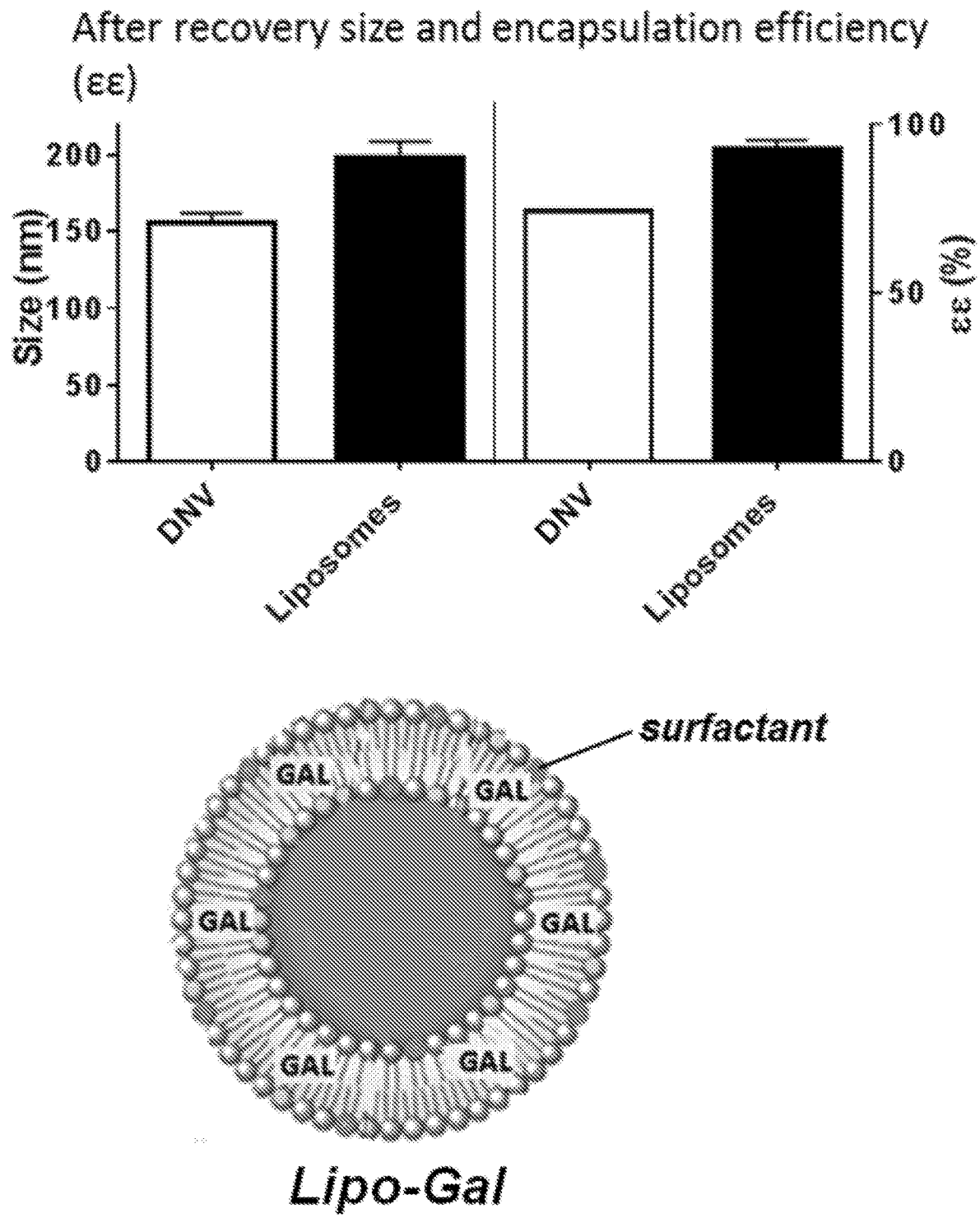
Fig. 10, cont'd.

DEFORMABLE NANO-SCALE VEHICLES (DNVS) FOR TRANS-BLOOD BRAIN BARRIER, TRANS-MUCOSAL, AND TRANSDERMAL DRUG DELIVERY

CROSS-REFERENCE TO RELATED APPLICATIONS

This application is a 371 US National Phase of PCT/US2016/062552, filed on Nov. 17, 2016, which claims benefit of and priority to U.S. Ser. No. 62/258,217, filed Nov. 20, 2015, both of which are incorporated herein by reference in their entirety for all purposes.

STATEMENT OF GOVERNMENTAL SUPPORT

[ Not Applicable]

BACKGROUND

Modern medicine affords us new drugs and associated delivery systems that can successfully treat various disease pathologies. However it is often the case that a drug is effective only at the target site and ineffective or even toxic in systemic circulation. A localized drug delivery system thus would have the potential to reduce the dosage and increase the efficacy of otherwise toxic drugs, and reduce or eliminate adverse effects, resulting in increased patient compliance and outcomes.

There are over 19 approved transdermal drug delivery systems and several experimental ones including patches, microneedles, plastic polymer and lipid nanoparticles and hydrogel matrices (Prausnitz et al. (2008) *Nat. Biotechnol.*, 26(11): 1261-268; Petelin et al. (1998) *Int. J Pharmaceut.* 173(1-2): 193-202; Madhav et al. (2012) *Exp. Opin. Drug Deliv.*, 9(6): 629-647; Patel et al. (2011) *J. Control. Rel.* 153(2): 106-116). These systems often suffer from failures in improvement of transport, safety and efficacy.

SUMMARY

In various embodiments deformable nano-scale vehicles (DNV) are provided that are useful for the delivery of therapeutic agents. In certain embodiments the DNVs are capable of transdermal delivery and can additionally cross the blood-brain barrier.

Various embodiments contemplated herein may include, but need not be limited to, one or more of the following:

Embodiment 1: A deformable nanoscale drug delivery vehicle, said vehicle comprising: one or more amphipathic vesicle-forming lipids; cholesterol; and a non-ionic detergent.

Embodiment 2: The nanoscale drug delivery vehicle of embodiment 1, wherein said amphipathic vesicle forming lipids comprise phospholipids.

Embodiment 3: The nanoscale drug delivery vehicle of embodiment 2, wherein said phospholipid is selected from the group consisting of 1,2-Dipalmitoyl-sn-glycero-3-phosphocholine (DPPC), N-(2,3-Dioleoyloxy-1-propyl), trimethylammonium (DOTAP), and 1,2-Dioleoyl-sn-glycero-3-phosphoethanolamine (DOPE).

Embodiment 4: The nanoscale drug delivery vehicle according to any one of embodiments 1-3, wherein said nanoscale drug delivery vehicle comprises a micelle.

Embodiment 5: The nanoscale drug delivery vehicle according to any one of embodiments 1-3, wherein said nanoscale drug delivery vehicle comprises a liposome.

Embodiment 6: The nanoscale drug delivery vehicle according to any one of embodiments 1-5, wherein said drug delivery vehicle comprises at least two phospholipids.

Embodiment 7: The nanoscale drug delivery vehicle according to any one of embodiments 2-6, wherein said phospholipid comprises DPPC and a second phospholipid.

Embodiment 8: The nanoscale drug delivery vehicle of embodiment 7, wherein the ratio of DPPC to said second phospholipid ranges from 2:1 to 1:2.

Embodiment 9: The nanoscale drug delivery vehicle of embodiment 7, wherein the ratio of DPPC to said second phospholipid is about 1:1.

Embodiment 10: The nanoscale drug delivery vehicle according to any one of embodiments 2-10, wherein the ratio of total phospholipid to cholesterol ranges from about 12:2 to about 5:4 or about 5:3, or from about 10:2 to about 6:2.

Embodiment 11: The nanoscale drug delivery vehicle of embodiment 10, wherein the ratio of phospholipid to second phospholipid to cholesterol is about 4:4:2.

Embodiment 12: The nanoscale drug delivery vehicle of embodiment 10, wherein the ratio of phospholipid to second phospholipid is about 5:3.

Embodiment 13: The nanoscale drug delivery vehicle according to any one of embodiments 1-12, wherein the w/w ratio of lipids (including cholesterol) to non-ionic detergent ranges from about 85:5 to about 85:25, or from about 85:10 to about 85:20.

Embodiment 14: The nanoscale drug delivery vehicle of embodiment 13, wherein the w/w ratio of lipids (including cholesterol) to detergent is about 85:15.

Embodiment 15: The nanoscale drug delivery vehicle according to any one of embodiments 1-14, wherein said non-ionic detergent comprises a detergent selected from the group consisting of Span 80, Tween 20, BRIJ® 76 (stearyl poly(10)oxy ethylene ether), BRIJ® 78 (stearyl poly(20) oxyethylene ether), BRIJ® 96 (oleyl poly(10)oxy ethylene ether), and BRIJ® 721 (stearyl poly (21) oxyethylene ether).

Embodiment 16: The nanoscale drug delivery vehicle of embodiment 15, wherein said drug delivery vehicle comprises about 10% to about 20%, or about 15% Span 80 by weight.

Embodiment 17: The nanoscale drug delivery vehicle according to any one of embodiments 1-15, wherein said nanoscale drug delivery vehicle is neutral (uncharged).

Embodiment 18: The nanoscale drug delivery vehicle of embodiment 17, wherein said phospholipid comprises DPPC and DOPE.

Embodiment 19: The nanoscale drug delivery vehicle according to any one of embodiments 1-5, wherein said nanoscale drug delivery vehicle is cationic.

Embodiment 20: The nanoscale drug delivery vehicle of embodiment 19, wherein said phospholipid comprises DPPC and DOTAP.

Embodiment 21: The nanoscale drug delivery vehicle according to any one of embodiments 1-5, wherein said nanoscale drug delivery vehicle is anionic.

Embodiment 22: The nanoscale drug delivery vehicle of embodiment 21, wherein said phospholipid comprises DPPC and DHP.

Embodiment 23: The nanoscale drug delivery vehicle according to any one of embodiments 1-22, wherein said vehicle (DNV) is not spherical in shape.

Embodiment 24: The nanoscale drug delivery vehicle according to any one of embodiments 1-23, wherein said vehicle (DNV) is an irregular shape.

Embodiment 25: The nanoscale drug delivery vehicle according to any one of embodiments 1-24, wherein said vehicle (DNV) is stable and able to be reconstituted to a functional DNV after storage as a lyophilized powder for at least 1 week, or at least 2 weeks, or at least 3 weeks, or at least 4 weeks, or at least 2 months, or at least 3 months, or at least 4 months, or at least 5 months, or at least 6 months, or at least 9 months, or at least 12 months, or at least 18 months, or at least 24 months.

Embodiment 26: The nanoscale drug delivery vehicle according to any one of embodiments 1-25, wherein said nanoscale drug delivery vehicle is functionalized with a polymer to increase serum halflife.

Embodiment 27: The nanoscale drug delivery vehicle of embodiment 26, wherein said polymer comprises polyethylene glycol and/or a cellulose or modified cellulose.

Embodiment 28: The nanoscale drug delivery vehicle according to any one of embodiments 1-27, wherein the DNVs range in size from about 50 nm up, or from about 60 nm, or from about 70 nm, or from about 80 nm, or from about 90 nm, or from about 100 nm, up to about 10 μm, or up to about 5 μm, or up to about 1 μm, or up to about 900 nm, or up to about 800 nm, or up to about 700 nm, or up to about 600 nm, or up to about 500 nm, or up to about 400 nm, or up to about 300 nm average diameter.

Embodiment 29: The nanoscale drug delivery vehicle according to any one of embodiments 1-27, wherein the DNVs range in size from about 50 nm up to about 275 nm average diameter.

Embodiment 30: The nanoscale drug delivery vehicle according to any one of embodiments 1-27, wherein the DNVs are about 50 nm average diameter, or about 100 nm average diameter, or about 150 nm average diameter.

Embodiment 31: The nanoscale drug delivery vehicle according to any one of embodiments 1-30, wherein transferrin is attached to nanoscale drug delivery vehicle.

Embodiment 32: The nanoscale drug delivery vehicle according to any one of embodiments 1-30, wherein folic acid is attached to nanoscale drug delivery vehicle.

Embodiment 33: The nanoscale drug delivery vehicle according to any one of embodiments 1-32, wherein said nanoscale drug delivery vehicle is attached to an antibody or a ligand that binds to a cell surface marker.

Embodiment 34: The nanoscale drug delivery vehicle of embodiment 33, wherein said cell surface marker is a marker of tumor cells.

Embodiment 35: The nanoscale drug delivery vehicle of embodiment 34, wherein said cell surface maker comprises a marker in Table 1.

Embodiment 36: The nanoscale drug delivery vehicle according to any one of embodiments 1-35, wherein said nanoscale drug delivery vehicle contains a cytotoxic and/or cytostatic agent.

Embodiment 37: The nanoscale drug delivery vehicle of embodiment 36, wherein said cytotoxic and/or cytostatic agent is selected from the group consisting of a IDH1 inhibitor, microtubule inhibitor, a DNA-damaging agent, and a polymerase inhibitor.

Embodiment 38: The nanoscale drug delivery vehicle of embodiment 37, wherein the cytotoxic or cytostatic agent comprises a tubulin inhibitor.

Embodiment 39: The nanoscale drug delivery vehicle of embodiment 38, wherein the cytotoxic or cytostatic agent comprises a drug selected from the group consisting of an auristatin, Dolastatin-10, synthetic derivatives of the natural product Dolastatin-10, and maytansine or a maytansine derivative.

Embodiment 40: The nanoscale drug delivery vehicle of embodiment 38, wherein the cytotoxic or cytostatic agent comprises a drug selected from the group consisting Monomethylauristatin F (MMAF), Auristatin E (AE), Monomethylauristatin E (MMAE), vcMMAE, and vcMMAF.

Embodiment 41: The nanoscale drug delivery vehicle of embodiment 38, wherein the cytotoxic or cytostatic agent comprises a maytansine selected from the group consisting of Mertansine (DM1), DM3, and DM4.

Embodiment 42: The nanoscale drug delivery vehicle of embodiment 37, wherein the cytotoxic or cytostatic agent comprises a DNA-damaging agent.

Embodiment 43: The nanoscale drug delivery vehicle of embodiment 42, wherein the cytotoxic or cytostatic agent comprises a drug selected from the group consisting of a calicheamicin, a duocarmycin, and a pyrrolobenzodiazepines.

Embodiment 44: The nanoscale drug delivery vehicle of embodiment 43, wherein the cytotoxic or cytostatic agent comprises a calicheamicin or a calicheamicin analog.

Embodiment 45: The nanoscale drug delivery vehicle of embodiment 43, wherein the cytotoxic or cytostatic agent comprises a duocarmycin.

Embodiment 46: The nanoscale drug delivery vehicle of embodiment 45, wherein the cytotoxic or cytostatic agent comprises a duocarmycin, selected from the group consisting of duocarmycin A, duocarmycin B1, duocarmycin B2, duocarmycin C1, duocarmycin C2, duocarmycin D, duocarmycin SA, Cyclopropylbenzoindole duocarmycin (CC-1065), Centanamycin, Rachelmycin, Adozelesin, Bizelesin, and Carzelesin.

Embodiment 47: The nanoscale drug delivery vehicle of embodiment 43, wherein the cytotoxic or cytostatic agent comprises a pyrrolobenzodiazepine or a pyrrolobenzodiazepine dimer.

Embodiment 48: The nanoscale drug delivery vehicle of embodiment 47, wherein the cytotoxic or cytostatic agent comprise a drug selected from the group consisting of Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

Embodiment 49: The nanoscale drug delivery vehicle of embodiment 36, wherein said cytotoxic and/or cytostatic agent comprises a drug is selected from the group consisting of auristatin, dolastatin, colchicine, combretastatin, and mTOR/PI3K inhibitors.

Embodiment 50: The nanoscale drug delivery vehicle of embodiment 36, wherein said cytotoxic and/or cytostatic agent comprises a drug selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-1 nitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thio-TEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

Embodiment 51: The nanoscale drug delivery vehicle of embodiment 36, wherein said cytotoxic and/or cytostatic agent comprises a cytotoxin.

Embodiment 52: The immunoconjugate of embodiment 51, wherein said antibody is attached to a cytotoxin selected from the group consisting of a Diphtheria toxin, a Pseudomonas exotoxin, a ricin, an abrin, saporin, and a thymidine kinase.

Embodiment 53: The nanoscale drug delivery vehicle according to any one of embodiments 1-35, wherein said DNV contains an inhibitor of an amyloidogenic pathway or an agent that switches APP processing from an amyloidogenic to a non-amyloidogenic pathway.

Embodiment 54: The nanoscale drug delivery vehicle of embodiment 53, wherein said DNV contains an agent selected from the group consisting of APP or eAPP, galangin, disulfiram and/or analogues thereof, honokiol and/or analogues thereof, tropisetron and/or analogues thereof, nimetazepam and/or analogues thereof, tropinol-esters and/or related esters and/or analogues thereof, TrkA kinase inhibitors (e.g., ADDN-1351) and/or analogues thereof, D2 receptor agonists, alpha 1-adrenergic receptor antagonists, and APP-specific BACE inhibitors including, but not limited to galangin, a galangin prodrug, rutin, a rutin prodrug, and other flavonoids and flavonoid prodrugs, and a hydantoin (e.g., as described in WO 2014127042 (PCT/PCT/US14/016100) which is incorporated herein by reference for the hydantoins described therein.

Embodiment 55: A pharmaceutical formulation comprising a nanoscale drug delivery vehicle according to any one of embodiments 1-54 and a pharmaceutically acceptable carrier.

Embodiment 56: The formulation of embodiment 55, wherein said formulation is compounded for delivery by route selected from the group consisting of oral delivery, isophoretic delivery, subdermal delivery, transdermal delivery, parenteral delivery, aerosol administration, administration via inhalation, intravenous administration, and rectal administration.

Embodiment 57: The formulation of embodiment 56, wherein said formulation is compounded for oral administration.

Embodiment 58: The formulation of embodiment 56, wherein said formulation is compounded for transdermal administration.

Embodiment 59: The formulation of embodiment 58, wherein said formulation is provided as a transdermal patch.

Embodiment 60: The formulation of embodiment 56, wherein said formulation is compounded for systemic administration.

Embodiment 61: The formulation according to any one of embodiments 55-60, wherein said formulation is a unit dosage formulation.

Embodiment 62: A method of delivery a therapeutic and/or imaging agent to a subject, said method comprising administering to said subject a nanoscale drug delivery vehicle according to any one of embodiments 1-35, wherein said nanoscale delivery vehicle contains said therapeutic and/or imaging agent.

Embodiment 63: The method of embodiment 62, wherein said nanoscale delivery vehicle is a nanoscale delivery vehicle according to any one of embodiments 36-54.

Embodiment 64: The method according to any one of embodiments 62-63, wherein said subject is a human.

Embodiment 65: The method according to any one of embodiments 62-63, wherein said subject is a non-human mammal.

Embodiment 66: The method according to any one of embodiments 62-65, wherein said nanoscale drug delivery vehicles are delivered via a route selected from the group consisting of oral delivery, isophoretic delivery, subdermal delivery, transdermal delivery, parenteral delivery, aerosol administration, administration via inhalation, intravenous administration, and rectal administration.

Embodiment 67: The method according to any one of embodiments 62-65, wherein said nanoscale drug delivery vehicles deliver a cargo across the blood-brain barrier.

Embodiment 68: The method of embodiment 67, wherein said nanoscale drug delivery vehicles are applied transdermally and deliver a cargo across the blood brain barrier.

Embodiment 69: The method according to any one of embodiments 62-65, wherein said nanoscale drug delivery vehicles deliver a cargo locally to craniofacial and/or oral bone.

Embodiment 70: The method of embodiment 69, wherein said nanoscale drug delivery vehicles deliver a cargo to alveolar bone.

Embodiment 71: The method according to any one of embodiments 62-65, wherein said nanoscale drug delivery vehicles deliver a cargo locally to a topical, intradermal, or subdermal site.

Embodiment 72: The method according to any one of embodiments 62-65, wherein said nanoscale drug delivery vehicles deliver a cargo to calvarial skin and/or to underlying bone.

Embodiment 73: The method according to any one of embodiments 62-65, wherein said nanoscale drug delivery vehicles are applied to the oral mucosa.

Embodiment 74: A method of making a deformable nanoscale drug delivery vehicle according to any one of embodiments 1-35, said method comprising: combining DNV building blocks in organic and aqueous phases in microchannels at a controlled flow ratio and pressure; and collecting the resulting samples containing DNVs.

Embodiment 75: The method of embodiment 74, wherein the samples are dialyzed to produce a dialyzed sample.

Embodiment 76: The method according to any one of embodiments 74-75, wherein the dialized sample is lyophilized to a powder.

Definitions

The terms "subject", "individual", and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The term "formulation" or "drug formulation" or "dosage form" or "pharmaceutical formulation" as used herein refers to a composition containing at least one therapeutic agent or medication for delivery to a subject. In certain embodiments the dosage form comprises a given "formulation" or "drug formulation" and may be administered to a patient in the form of a lozenge, pill, tablet, capsule, suppository, membrane, strip, liquid, patch, film, gel, spray or other form.

BRIEF DESCRIPTION OF THE DRAWINGS

FIG. 5A shows an image of the application site on the mouse oral mucosa. FIG. 5B shows an LAS-3000 image of excised gingival tissue 48 h post application. Note site (ii) exhibits minimal fluorescence, suggesting high permeation of applied loaded DNVs. FIG. 5C shows an LAS-3000 image of alveolar bone underlying the application site, showing that DNVs permeated through oral mucosa and delivered bone-targeting fluorescent tag, without systemic leakage, as indicated by unlabeled femur bones.

FIG. 7A is an image showing application site; shaved skin above the skull, between the ears. FIG. 7B shows an LAS-3000 fluorescent image of excised calvarial skin from mice 48 hours after application.

DETAILED DESCRIPTION

Figure 1A:
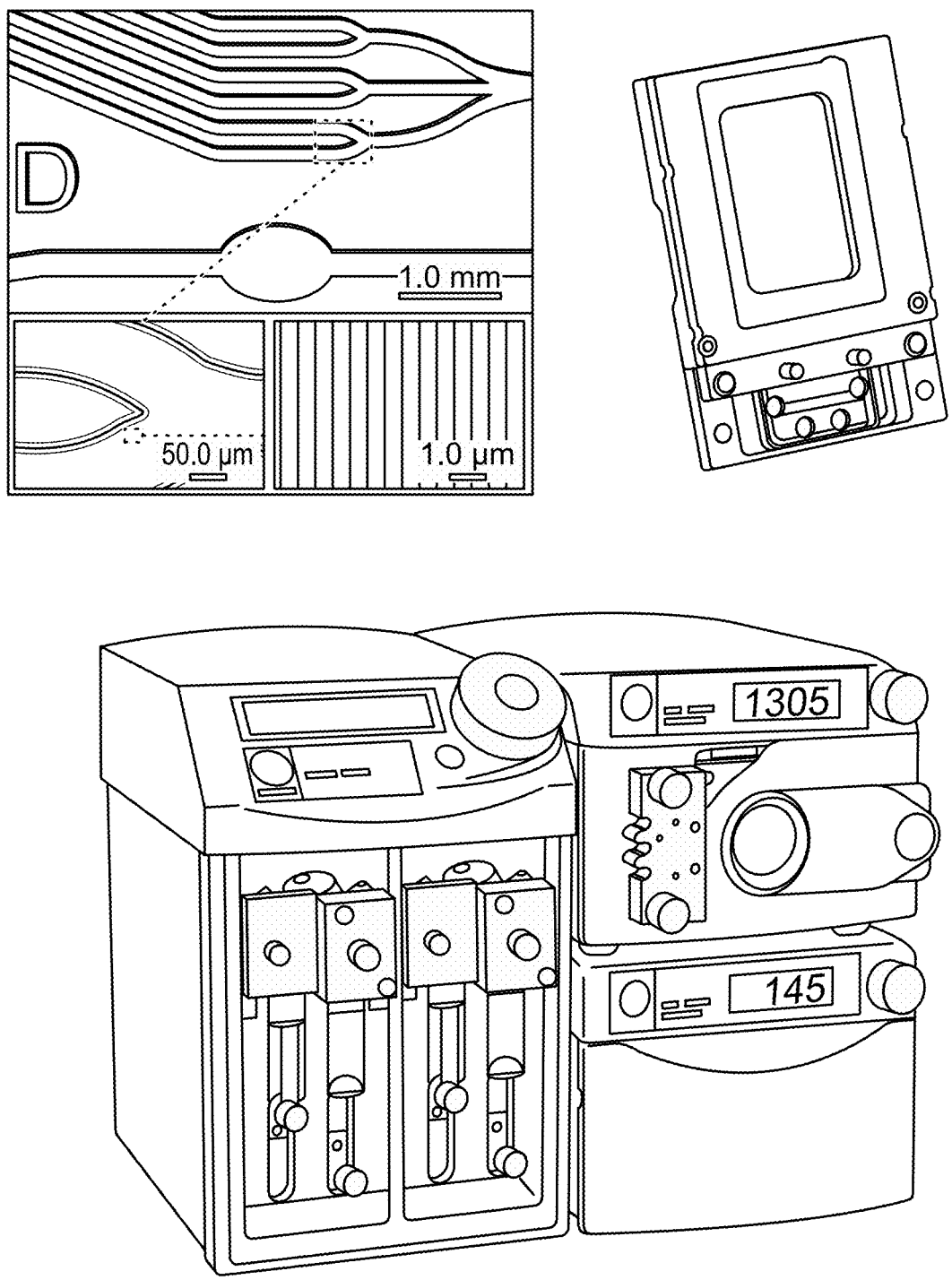
FIG. 1A illustrates one embodiment of devices used to fabricate DNVs. Microfluidic channels are shown top left. A microfluidic reactor is shown (top right) along with a microfluidic reactor system (bottom).

In various embodiments deformable nano-scale vehicles (DNV) are provided that are useful for the delivery of therapeutic agents. In certain embodiment the deformable nano-scale vehicles (DNVs) are elastic nanoparticles, composed of phospholipids such as 1,2-dipalmitoyl-sn-glycero-3-phosphocholine (DPPC), N-(2,3-dioleoyloxy-1-propyl) trimethylammonium (DOTAP), and/or 1,2-dioleoyl-sn-glycero-3-phosphoethanolamine (DOPE). In various embodiments, in addition to phospholipids, DNVs contain cholesterol which can act as a membrane regulator, and a non-ionic detergent which can act as an edge activator (illustrative, but non-limiting formulations use Span 80 (also known as sorbitan laurate, or sorbitan monolaurate) and/or Tween 20 (also known as polyethylene glycol sorbitan monolaurate, or polyoxyethylenesorbitan monolaurate) that confers deformability to the lipid bilayer of the nanoparticle.

In various embodiments the DNVs described herein are capable of crossing the blood-brain barrier (BBB) and can be used to deliver a cargo (e.g., one or more therapeutic agent(s) as described herein) to the brain/CNS. Such delivery across the blood-brain barrier can be accomplished by administration of the DNVs according to any of a number of modalities including, but not limited to, aerosol administration including nasal inhalation, oral inhalation, and the like, oral delivery, isophoretic delivery, subdermal delivery, transdermal delivery, parenteral delivery, intravenous administration, intra-arterial administration, depot delivery, and rectal administration.

In certain embodiments the DNVs are provided in transdermal patches for delivery of cargo across the blood-brain barrier (BBB) to the central nervous system (CNS). In addition to methods of synthesizing the DNVs themselves, transdermal patches loaded with CNS-targeted DNVs for delivery of cargo (drugs, proteins, antibodies, RNA or DNA) to the brain are provided.

In certain embodiments the DNVs can be provided as patch, capsule, liquid (and the like) for non-CNS localized delivery of DNVs. In some cases, very localized non-CNS delivery is required for effective treatment, with avoidance of systemic distribution of DNVs. DNVs with increased charge and therefore restricted distribution can be synthesized.

In certain embodiments targeted DNVs are contemplated. Both inside and outside of the CNS it may be desirable to limit deliver of the cargo (drug, protein, etc.) to a specific cell type, for example a tumor cell. Accordingly DNVs are provided that are decorated on the exterior with ligands that interact specifically with a target cell, for example folic acid to target FA receptor-expressing cells or transferrin (Tf) to interact with the transferrin receptor on the BBB. Other illustrative targets are shown below in Table 1.
DNVs.

In various embodiments the DNVs contemplated herein comprise one or more vesicle-forming lipids, generally including amphipathic lipids having both hydrophobic tail groups and polar head groups, cholesterol, and a detergent. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. In certain embodiments a vesicle-forming lipid for use in the DNVs may include any conventional lipid possessing one of the characteristics described above.

In certain embodiments the vesicle-forming lipids of this type are those having two hydrocarbon tails or chains, typically acyl groups, and a polar head group. Included in this class are the phospholipids, such as phosphatidylcholine (PC), phosphatidylethanolamine (PE), phosphatidic acid (PA), phosphatidylglycerol (PG), and phosphatidylinositol (PI), where the two hydrocarbon chains are typically between about 14-22 carbon atoms in length, and have varying degrees of unsaturation. In certain embodiments suitable phospholipids include PE and PC. One illustrative PC is hydrogenated soy phosphatidylcholine (HSPC). Single chain lipids, such as sphingomyelin (SM), and the like can also be used. In certain embodiments the phospholipids comprise one or more phospholipids such as 1,2-Dipalmitoyl-sn-glycero-3-phosphocholine (DPPC), N-(2,3-Dioleoyloxy-1-propyl) trimethylammonium (DOTAP), and/or 1,2-Dioleoyl-sn-glycero-3-phosphoethanolamine (DOPE).

The above-described lipids and phospholipids whose acyl chains have a variety of degrees of saturation can be obtained commercially, or prepared according to published methods. Other lipids that can be included in certain embodiments are sphingolipids and glycolipids. The term "sphingolipid" as used herein encompasses lipids having two hydrocarbon chains, one of which is the hydrocarbon chain of sphingosine. The term "glycolipids" refers to shingolipids comprising also one or more sugar residues.

In various embodiments the DNVs additionally include lipids that can stabilize the a DNV composed predominantly of phospholipids. An illustrative lipid of this group is cholesterol at levels between 20 to 45 mole percent.

In various embodiments the DNVs, can further include a surface coating of a hydrophilic polymer chain. In certain embodiments the hydrophilic polymer can be included in the DNV by including in the DNV composition one or more lipids (e.g., phospholipids) derivatized with a hydrophilic polymer chain which can be used include, but are not limited to any of those described above, however, in certain embodiments, vesicle-forming lipids with diacyl chains, such as phospholipids, are preferred. One illustrative phospholipid is phosphatidylethanolamine (PE), which contains a reactive amino group convenient for coupling to the activated polymers which can be coupled with targeting molecules such as transferrin, folic acid, and the like One illustrative PE is distearoyl PE (DSPE). Another example is non-phospholipid double chain amphiphilic lipids, such as diacyl- or dialkylglycerols, derivatized with a hydrophilic polymer chain.

In certain embodiments a hydrophilic polymer for use on a DNV to increase serum halflife and/or for coupling an antibody or ligand is polyethyleneglycol (PEG), in certain embodiments as a PEG chain having a molecular weight between 1,000-10,000 Daltons, or between 1,000-5,000 Daltons, or preferably between 2,000-5,000 Daltons. Methoxy or ethoxy-capped analogues of PEG are also useful hydrophilic polymers, commercially available in a variety of polymer sizes, e.g., 120-20,000 Daltons.

Other hydrophilic polymers that can be suitable include, but are not limited to polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose.

Preparation of lipid-polymer conjugates containing these polymers attached to a phospholipid have been described, for example in U.S. Pat. No. 5,395,619. In certain embodiments, typically, between about 0.1-20 mole percent of the polymer-derivatized lipid is included in the liposome-forming components during liposome formation. Polymer-derivatized lipids are also commercially available (e.g. SUN-BRITE(R), NOF Corporation, Japan.).

In various embodiments the hydrophilic polymer chains provide a surface coating of hydrophilic chains sufficient to extend the blood circulation time of the DNVs in the absence of such a coating.

In one illustrative an non-limiting embodiment, the lipids (including cholesterol) and the edge activator are present in an 85:15 w/w ratio.

The exact molar ratio and types of lipid components used are determined based on the intended application of the DNVs. For example, for trans-oral mucosal and trans-dermal topical application, in one illustrative, but non-limiting embodiment, a 5:3:2 molar ratio (DPPC:Cholesterol:DOTAP) is used, with the mixture containing 15% Span 80 by weight.

These components, dissolved in an organic solvent such as isopropyl alcohol (IPA) are combined with aqueous solution (PBS or DI water) via separate inputs into a microfluidic reactor system for efficient and continuous synthesis at a temperature ranging from 25° C. to 40° C. and 1 bar pressure. The microfluidic reactor channels provide high shear stress and controlled mixing, with minimized turbulence, resulting in well-defined DNV populations, and eliminating the need for post-processing such as sonication or extrusion to obtain appropriate or uniform size. Upon transitioning from organic to aqueous phase, the components described self-configure into DNVs, according to their thermodynamic stability in aqueous solvent. They are non-toxic, prepared with high reproducibly with little batch to batch variability, scalable, very homogenous in population and distribution, of tunable size, and provide highly localized payload delivery. Our research shows that this method can produce homogenous DNV populations with sizes from 50 nm to the micron range.

In certain embodiments the DNVs range in size from about 50 nm up, or from about 60 nm, or from about 70 nm, or from about 80 nm, or from about 90 nm, or from about 100 nm, up to about 10 µm, or up to about 5 µm, or up to about 1 µm, or up to about 900 nm, or up to about 800 nm, or up to about 700 nm, or up to about 600 nm, or up to about 500 nm, or up to about 400 nm, or up to about 300 nm average diameter. In certain embodiments the DNVs range in size from about 50 nm up to about 275 nm average diameter. In certain embodiments the DNVs are about 50 nm average diameter, or about 100 nm average diameter, or about 150 nm average diameter, or about 200 nm average diameter or about 250 nm average diameter.

Resultant DNV size can be tuned primarily by the adjustment of the flow rate ratio (FRR) between the aqueous phase and the organic, lipid containing, phase. Our investigations have shown that increasing the flow rate ratio directly decreases resultant DNV size as well as reducing size variability. For trans-oral mucosal and topical application, a FRR of 100 is used, to obtain DNVs with a size centered at 250 nm from the aforementioned components. Note that the same FRR may produce different sized DNVs, depending on the particular types of components used.

The DNVs can be synthesized to encapsulate various classes of drugs, including, but not limited to, small molecules, as well as proteins, RNA, and DNA. They can efficiently encapsulate both hydrophilic and hydrophobic drugs or other cargo. We can successfully synthesize DNVs encapsulating, inter alia, hydrophilic drugs such as fluorescein derivative, DNVs containing fluorescein isothiocyanate (FITC), and/or a fluorescently-tagged bone targeting drug or drugs with no tags. In the case of hydrophobic drugs, we actively use DNVs to encapsulate molecules with low water solubility such as but not limited to galangin. In case of proteins we actively use DNVs to encapsulate proteins such as but not limited to sAPPalpha and BDNF or in case of nucleic acids we actively use DNVs to encapsulate nucleic acids such as but not limited to miRNAs that affect disease targets in the brain. These DNVs are synthesized to be delivered through the blood brain barrier (trans-BBB delivery). The solubility of a given drug dictates the phase (organic or aqueous) that it is introduced in to the microfluidic reactor, with highest encapsulation when both drug and DNV components are in the same (organic) phase.

Another important tunable feature on the DNVs is charge. The charge on the DNVs will, in part, determine the degree of dispersion from the application site. DNVs of various charge concentrations (zeta potentials) can be created through the use of different combinations of charged phospholipid components. We have synthesized neutral (DPPC, cholesterol, DOPE), cationic (DPPC, cholesterol, DOTAP) and anionic (DPPC,cholesterol,DHP) DNVs. The amount of charge can be tuned by adjusting the concentration of a particular charged component in the DNV preparation mixture. By tuning charge, DNV delivery can be restricted to local delivery or permitted to allow systemic delivery.

In addition to size, cargo, deformability, and charge the half-life of DNVs can be increased by additional of polyethylene glycol (PEG) or other polymers. Depending upon the therapeutic goal, addition of PEG is an option.

Targeted DNVs.

In addition to cargo, size, and deformability, DNVs may be synthesized that are "decorated" on the exterior with targeting agents such as, but not limited to, transferrin or folic acid to allow targeting of cells that express transferrin ((Tf) or folic acid receptors, respectively. These receptors are often expressed on the BBB or tumor cells and therefore DNV with these targeting agents could bind and cross the BBB and these cells can be targeted. Other cell types may specifically be targeted by use of other ligands on the DNV surface.

Generally, the targeting agents can associate with any target of interest, such as a target associated with an organ, tissues, cell, extracellular matrix or intracellular region. In certain embodiments, a target can be associated with a particular disease state, such as a cancerous condition. In some embodiments, the targeting agent can be specific to only one target, such as a receptor. Suitable targets can include, but are not limited to, a nucleic acid, such as a DNA, RNA, or modified derivatives thereof. Suitable targets can also include, but are not limited to, a protein, such as an extracellular protein, a receptor, a cell surface receptor, a tumor-marker, a transmembrane protein, an enzyme or an antibody. Suitable targets can include a carbohydrate, such as a monosaccharide, disaccharide or polysaccharide that can be, for example, present on the surface of a cell.

In certain embodiments, a targeting agent can include a target ligand (e.g., an RGD-containing peptide), a small molecule mimic of a target ligand (e.g., a peptide mimetic ligand) or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. In certain embodiments the targeting agents can also include an aptamer. Aptamers can be designed to associate with or bind to a target of interest. Aptamers can be comprised of, for example, DNA, RNA and/or peptides, and certain aspects of aptamers are well known in the art (see, e.g., Klussman, S., Ed., The Aptamer Handbook, Wiley-VCH (2006); Nissenbaum (2008) *Trends in Biotech.* 26(8): 442-449; and the like).

In certain embodiments the DNV is attached to a ligand or antibody that binds to a cell surface marker. In certain embodiments the marker is a tumor marker and the antibody/ligand can serve to direct/localize the DNV at a cancer cell (e.g., a tumor site).

An illustrative, but not limiting list of suitable tumor markers is provided in Table 1. Antibodies to these and other cancer markers are known to those of skill in the art and can be obtained commercially or readily produced, e.g. using phage-display technology.

TABLE 1

Illustrative cancer markers and associated references, all of which are incorporated herein by reference for the purpose of identifying the referenced tumor markers.

| Marker | Reference |
| --- | --- |
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmann et al. (1997) *Oncol Res.*, 9(3) 119-127 |
| APRIL | Sordat et al. ('998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-abl (b3a2) | Verfaillie et al. ('996) *Blood*, 87(11): 4770-4779 |
| CA-125 | Bast et al. ('998) *Int J Biol Markers*, 13(4): 179-187 |
| CASP-8/FLICE | Mandruzzato et al. (1997) *J Exp Med.*, 186(5): 785-793. |
| Cathepsins | Thomssen et al. (1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |

TABLE 1-continued

Illustrative cancer markers and associated references, all of which are incorporated herein by reference for the purpose of identifying the referenced tumor markers.

| Marker | Reference |
| --- | --- |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al. (1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al. (1996) *Melanoma Res.*, 6(1): 11-24 |
| gp75/TRP-1 | Lewis et al. (1995) *Semin Cancer Biol.*, 6(6): 321-327 |
| hCG | Hoermann et al. (1992) *Cancer Res.*, 52(6): 1520-1524 |
| Heparanase | Vlodavsky et al. (1999) *Nat Med.*, 5(7): 793-802 |
| Her2/neu | Lewis et al. (1995) *Semin Cancer Biol.*, 6(6): 321-327 |
| Her3 | |
| HMTV | Kahl et al. (1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/MART-1 | Lewis and Houghton (1995) *Semin Cancer Biol.*, 6(6): 321-327 |
| mesothelin | Chang et al. (1996) *Proc. Natl. Acad. Sci., USA*, 93(1): 136-140 |
| MIC A/B | Groh et al. (1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |

TABLE 1-continued

Illustrative cancer markers and associated references, all of which are incorporated herein by reference for the purpose of identifying the referenced tumor markers.

| Marker | Reference |
| --- | --- |
| p53 | Roth et al. (1996) *Proc. Natl. Acad. Sci., USA*, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al. (1997) *Cancer Res.*, 57(12): 2321-2324 |
| RAGE-1 | Gaugler et al. (1996) *Immunogenetics*, 44(5): 323-330 |
| Rb | Dosaka-Akita et al. (1997) *Cancer*, 79(7): 1329-1337 |
| RCAS1 | Sonoda et al. (1996) *Cancer*, 77(8): 1501-1509. |
| SART-1 | Kikuchi et al. (1999(*Int J Cancer*, 81(3): 459-466 |
| SSX gene family | Gure et al. (1997) *Int J Cancer*, 72(6): 965-971 |
| STAT3 | Bromberg et al. (1999) *Cell*, 98(3): 295-303 |
| STn (mucin assoc.) | Sandmaier et al. (1999) *J Immunother.*, 22(1): 54-66 |
| TAG-72 | Kuroki et al. (1990)*Cancer Res.*, 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prey*, 7(6): 497-504 |
| Thymosin β 15 | Bao et al. (1996) *Nature Medicine.* 2(12), 1322-1328 |
| IFN-α | Moradi et al. (1993) *Cancer*, 72(8): 2433-2440 |
| TPA | Maulard et al. (1994) *Cancer*, 73(2): 394-398 |
| TPI | Nishida et al. (1984) *Cancer Res* 44(8): 3324-9 |
| TRP-2 | Parkhurst et al. (1998) *Cancer Res.*, 58(21) 4895-4901 |
| Tyrosinase | Kirkin et al. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et al. (1995) *Oncogene* Aug. 17, 1995; 11(4): 635-645 |
| Glutathione S-transferase | Hengstler (1998) et al. *Recent Results Cancer Res.*, 154: 47-85 |

Methods of coupling lipid-containing constructs and targeting agents are well known to those of skill in the art. Examples include, but are not limited to the use of biotin and avidin or streptavidin (see, e.g., U.S. Pat. No. 4,885,172 A), by traditional chemical reactions using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. Appropriate reactions which may be applied to such couplings are described in Williams et al. Methods in Immunology and Immunochemistry Vol. 1, Academic Press, New York 1967.

The DNVs described herein offer numerous advantages which include, but are not limited to the following:
1) The DNVs have the ability to increase localized drug delivery (i) through oral mucosa, (ii) into dermal layers, and (iii) transdermally;
2) The DNVs have the potential to allow or increases delivery of small molecules, proteins, RNAs, and/or antibodies through the blood brain barrier to the brain for CNS disorders;
3) The DNVs have the potential to deliver cargo specifically to targeted cells types, thus avoiding off-target or side effects.

The blood brain barrier (BBB) limits the therapeutic molecules that can be used for treatment of neurological disorders such as AD and PD. Having the capability to transport a variety of molecules including, but not limited to, small molecules, peptides, proteins, antibodies, aptamers, miRNA, and small molecule polymer conjugates, to the brain in DNVs increases the variety of therapeutics that could be evaluated and developed for treatment of these devastating disorders. Furthermore DNVs can facilitate delivery by numerous routes of administration, including the transdermal route, that could increase ease of dosing and compliance in an older or ill patient population. Additionally, targeted DNVs allow delivery of therapeutics only to certain cell types, thus limiting side effects.

It is believed that none of the existing liposomal technologies have been shown to effectively deliver therapeutics transdermally that then also cross the blood-brain barrier (BBB). Therapeutics for CNS disorders are limited by their ability to cross the BBB. This results in the exclusion of many potential novel therapeutics that could be evaluated and developed for CNS disorders. In addition, patient compliance is an obstacle for successful treatment. The DNVs described herein have the potential to enable a variety of molecules to be evaluated in the treatment of CNS disorders like AD and PD, thus increasing success in finding effective new therapeutics for such CNS disorders.

DNVs enable delivery of a larger class of molecules. Existing technologies are mostly limited to small molecules. DNVs have little to no toxicity, and in localized delivery, do not damage deeper viable tissue. The DNVs do not require ultrasound, electricity or chemical enhancers to be applied on the skin.

While there are number of liposome-based approaches for encapsulation and delivery of drugs primarily by the systemic route, the DNVs described herein for the first time provides the potential of using liposomal technology to generate DNVs to deliver drugs by the transdermal route for ultimate brain delivery. Furthermore the discovery that the DNVs described herein can be generated in a microreactor using the flow-chemistry apparatus allows for CNS-targeted drug-loaded elastic liposomes to be prepared with a high degree of quality control, very small and uniform diameter and potentially on a large scale.

Combinatorial Drug Delivery Platform

In certain embodiment, we can encapsulate two drugs in the liposome formulation. One of the drug could for example be but not limited to a kinase inhibitor such as masatinib or its analog that could protect against neuroinflammation and other drug could be but not limited to sAPPα enhancers.

Pharmaceutical Formulations.

In various embodiments pharmaceutical formulations contemplated herein generally contain DNVs as described herein and a pharmaceutically acceptable carrier. The term "carrier" typically refers to an inert substance used as a diluent or vehicle for the pharmaceutical formulation. The term can also encompass a typically inert substance that imparts cohesive qualities to the composition. Typically, the physiologically acceptable carriers are present in liquid form. Examples of liquid carriers include, but not limited to, physiological saline, phosphate buffer, normal buffered saline (135-150 mM NaCl), water, buffered water, 0.4% saline, 0.3% glycine, 0.3M sucrose (and other carbohydrates), glycoproteins to provide enhanced stability (e.g., albumin, lipoprotein, globulin, etc.) and the like. Since physiologically acceptable carriers are determined in part by the particular composition being administered as well as by the particular method used to administer the composition, there are a wide variety of suitable formulations of pharmaceutical compositions of the present invention (see, e.g., Remington's Pharmaceutical Sciences, Maak Publishing Company, Philadelphia, Pa., 17th ed. (1985)).

In various embodiments the pharmaceutical formulations can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. In certain embodiments the compositions can contain pharmaceutically acceptable auxiliary substances as required to approximate physiological conditions, such as pH adjusting and buffering agents, tonicity adjusting agents, wetting agents and the like, e.g., sodium acetate, sodium lactate, sodium chloride, potassium chloride, calcium chloride, sorbitan monolaurate and triethanolamine oleate. Sugars can also be included for stabilizing the compositions, such as a stabilizer for lyophilized compositions.

Pharmaceutical compositions suitable for parenteral administration, such as, for example, by intraarticular, intravenous, intramuscular, intratumoral, intradermal, intraperitoneal and subcutaneous routes, can include aqueous and non-aqueous, isotonic sterile injection solutions. In certain embodiments the injection solutions can contain antioxidants, buffers, bacteriostats and solutes that render the formulation isotonic with the blood of the intended recipient, and aqueous and non-aqueous sterile suspensions that can include suspending agents, solubilizers, thickening agents, stabilizers and preservatives. Injection solutions and suspensions can also be prepared from sterile powders, such as lyophilized liposomes. In certain embodiments the compositions can be administered, for example, by intravenous infusion, intraperitoneally, intravesically or intrathecally. In various embodiments parenteral administration and intravenous administration are also contemplated. The formulations of liposome compositions can be presented in unit-dose or multi-dose sealed containers, such as ampoules and vials.

In certain embodiments the pharmaceutical compositions are formulated for administration as an aerosol, e.g., for oral and/or nasal inhalation.

In certain embodiments the pharmaceutical compositions are formulated for topical deliver, intradermal delivery, subdermal delivery and/or transdermal delivery.

In certain embodiments the pharmaceutical compositions are formulate for application to oral mucosa, vaginal mucosa, and/or rectal mucosa.

In certain embodiments the pharmaceutical composition is in unit dosage form. In such form, the composition is subdivided into unit doses containing appropriate quantities of the active component, e.g., a DNV formulation. The unit dosage form can be a packaged composition, the package containing discrete quantities of the pharmaceutical composition. The composition can, if desired, also contain other compatible therapeutic agents.

In certain embodiments the DNVs described herein can be delivered through the skin using conventional transdermal drug delivery systems, i.e., transdermal "patches" wherein the active agent(s) (e.g., DNVs and/or formulations thereof) are typically contained within a laminated structure that serves as a drug delivery device to be affixed to the skin. In such a structure, the e.g., DNVs and/or formulations thereof is typically contained in a layer, or "reservoir," underlying an upper backing layer. It will be appreciated that the term "reservoir" in this context refers to a quantity of e.g., DNVs and/or formulations thereof that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the e.g., DNVs and/or DNV formulation reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) (e.g., DNVs and/or formulations thereof) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

EXAMPLES

The following examples are offered to illustrate, but not to limit the claimed invention.

Example 1

Preparation and Characterization of DNVs

We present here our investigations into one such technology: deformable nano-scale vehicles (DNVs). In various illustrative embodiments, the drug delivery vehicle is comprised of biologically-derived components, and multiple proprietary ingredients to confer deformability to the vehicles.

We have utilized a microfluidic reactor for the efficient and continuous synthesis of these DNVs. They are non-toxic, easy to prepare, scalable and highly reproducible, very homogenous in population and distribution, of controllable size, and provide highly localized payload delivery.

In various embodiments the DNVs described herein provide an efficient vehicle to deliver drugs locally to craniofacial and/or oral bone. As illustrated herein, in various embodiments, cationic DNVs were synthesized to carry a fluorescently tagged hydrophilic drug and were applied non-occluded to (i) the shaved scalp and (ii) the gingival surface in the oral cavity in mice (n=4) to test their permeability and drug flux. Our results show, as theorized, that the cationic DNVs are able to reach and deliver their payload to their target of alveolar bone in the case of oral application and to the skin layers upon dermal application, without any systemic payload leakage.

Materials

Microfluidic reactor system (FIG. 1A), 26 μL-1000 uL reactor chip, using a micromixer prior to entry in chip as shown in FIG. 1A. DI Water, PBS, isopropyl alcohol, chloroform, dialysis membranes, lyophilizer, DNV building blocks, including membrane components, membrane regulator and, deformability ingredients. Zetasizer (Malvern Z series), Dynamic Light Scatterer (Wyatt). Transmission Electron Microscope (JEOL). Mini-Extruder and membranes of 50 nm pore size (Avanti Polar Lipids). LAS-3000 (Fujifilm)

Figure 1B:
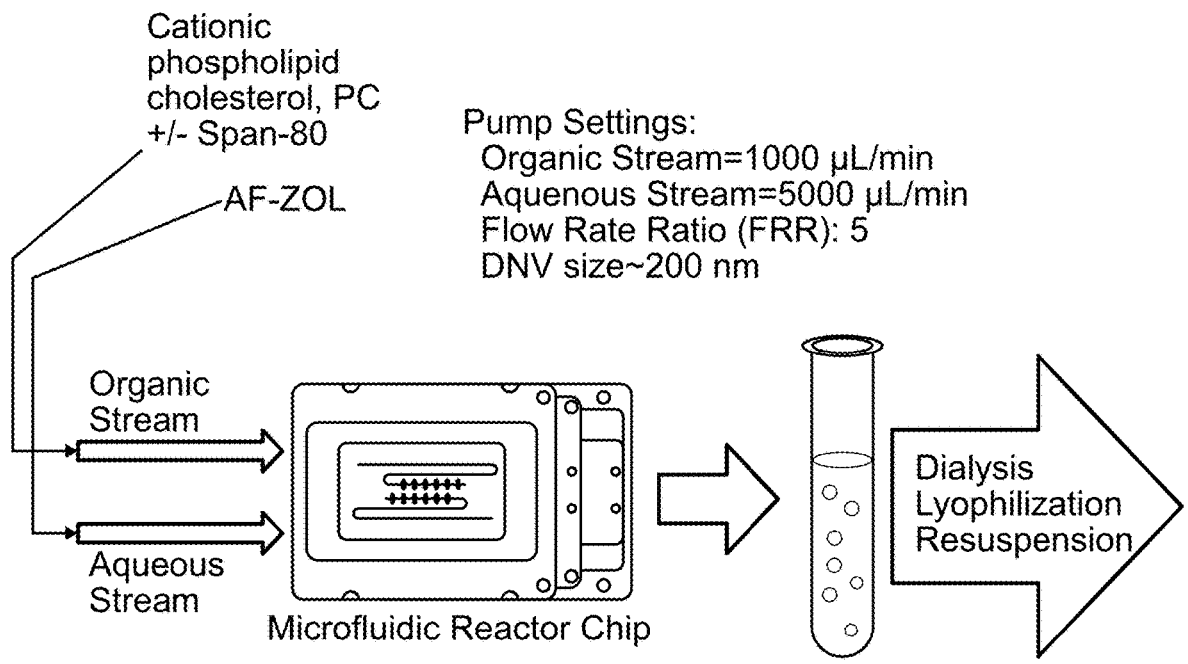
FIG. 1B illustrates the microfluidic synthesis scheme for preparation of the AF-ZOL DNV encapsulating the hydrophilic Zolodentrate
Figure 1B:
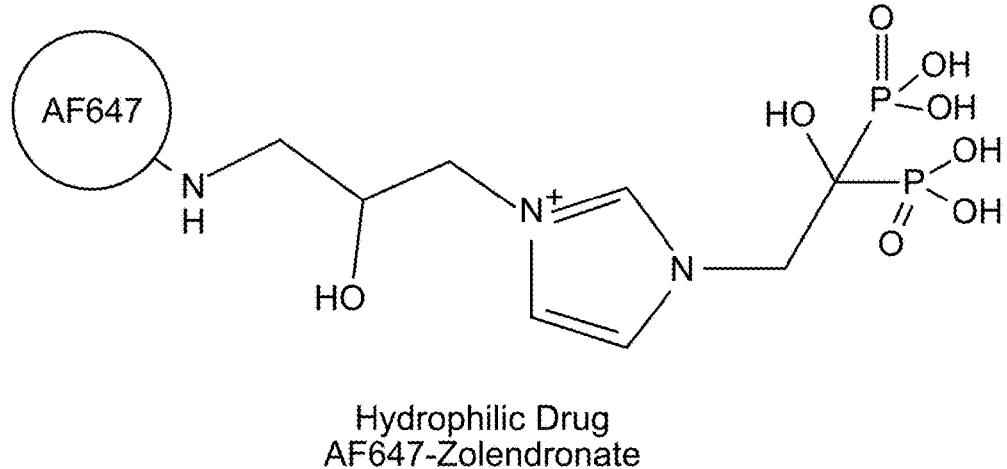

Preparation of Prototype DNVs:

The DNVs for transdermal delivery of AF647-Zoledronate (AF-ZOL), a fluorescent bisphosphonate, were prepared in a microfluidic reactor using the scheme shown in FIG. 1B combining building blocks in organic and aqueous phases at a precisely controlled flow rate ratio 5 was used as shown in FIG. 1B, at room temperature and pressure, providing high shear stress at a fast rate and controlled mixing in micro-channels, reducing turbulence and minimizing the size and dispersity of the resultant AF-ZOL DNVs.

Collected samples were then twice dialyzed overnight through a 20K membrane. Following dialysis, samples were lyophilized twice to a powder for long term storage, typically in liquid nitrogen (77 K). The DNVs can be resuspended in a final volume of 10 μL in an appropriate vehicle for topical and gingival application via direct pipette application on anesthetized mice or incorporated in a gel for application to the shaved Calvarial skin surface. Intended final clinical use in this domain is likely to be in the form of a pre-filled syringe, a swab or a gel patch.

Characterization:

Characterization of DNVs was performed using Atomic Force Microscopy (AFM), Transmission Electron Microscopy and the Malvern Zetasizer for electrical properties of empty and loaded DNVs.

Size—Size measurements, and dispersity analysis of DNVs were obtained through a zetasizer (Malvern Z series) and corroborated by Dynamic Light Scattering (Wyatt).

Zeta Potential—The zeta potential of the DNVs in suspension was obtained by zetasizer measurements (Malvern Z series).

Entrapment Efficiency—Separation of DNV encapsulated drug and free drug, by either ultracentrifugation (100,000 Gs @ 2 hr) or dialysis. Both supernatant and resuspended DNV solution analyzed via fluorescent spectrophotometry to provide a comparison of entrapped and free drug. Entrapment efficiency=(Total drug−free drug)* 100% For these studies, a fluorescein derivative, Fluorescein Isothiocyanate (FITC), was used.

Elasticity—Qualitative comparison of elasticity of differently formulated vehicles was performed with a mini-extruder, and membrane of 50 nm pore size. (Avanti Polar Lipids).

Figure 2:
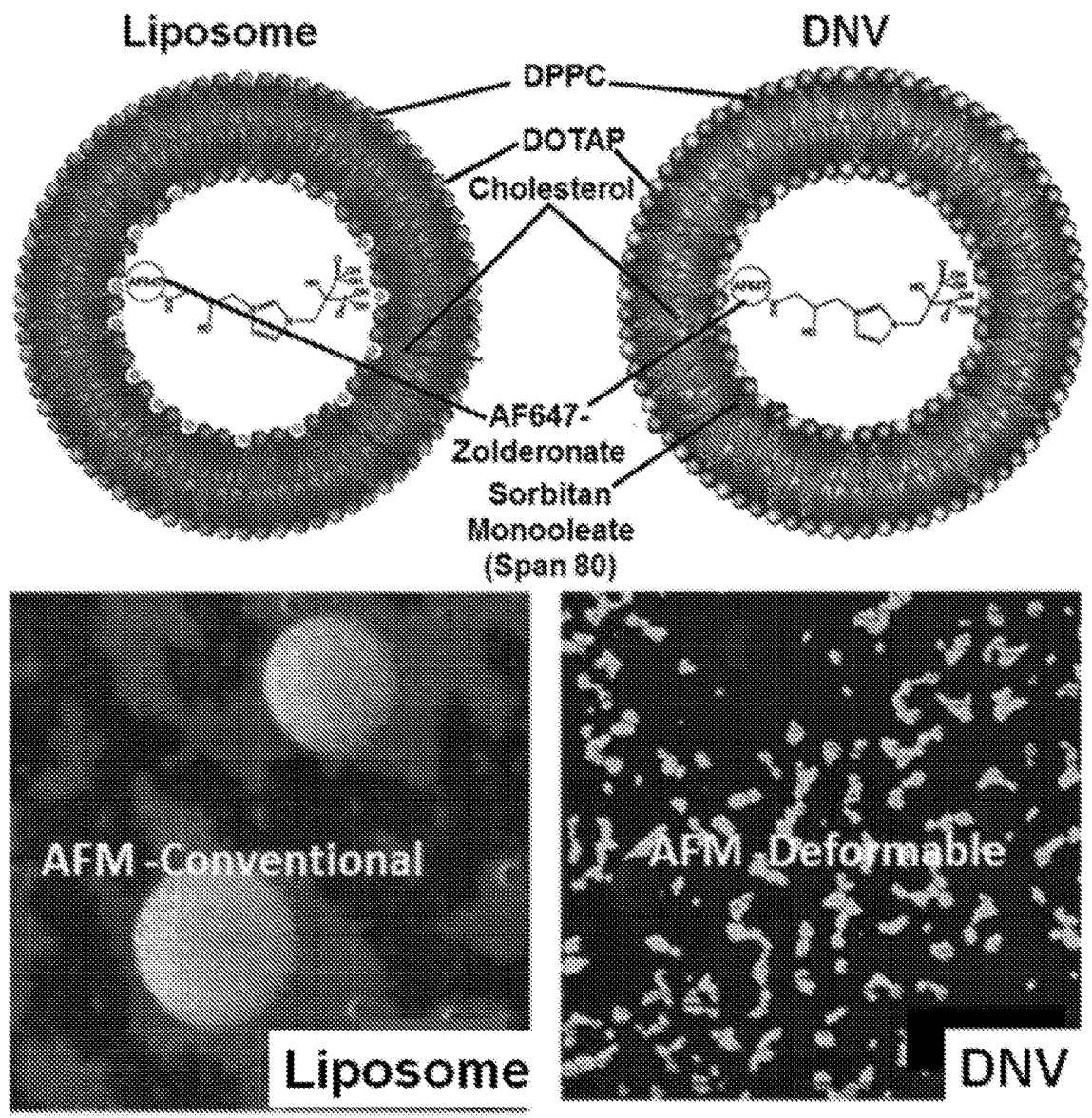
FIG. 2 illustrates visualization of deformable nano-scale vehicles. Deformable Nano-scale Vehicles (DNVs) loaded with drug, prepared on freshly cleaved mica and imaged in fluid, via Atomic Force Microscopy. The phase analysis shows that conventional liposome (nDNV) has a spherical shape while the DNV is deformed (not spherical) in shape.
Figure 3A:
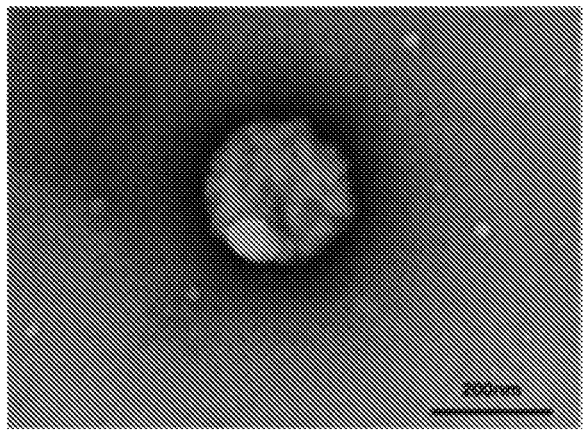
FIG. 3A shows a transmission electron microscope (TEM) image of a conventional liposome, and a DNV encapsulating the drug AF-ZOL produced by the microfluidic approach with a size of roughly 200 nm. At the bottom is a TEM image of the microfluidic produced DNV after weeks of storage as a lyophilized powder.
Figure 3A:
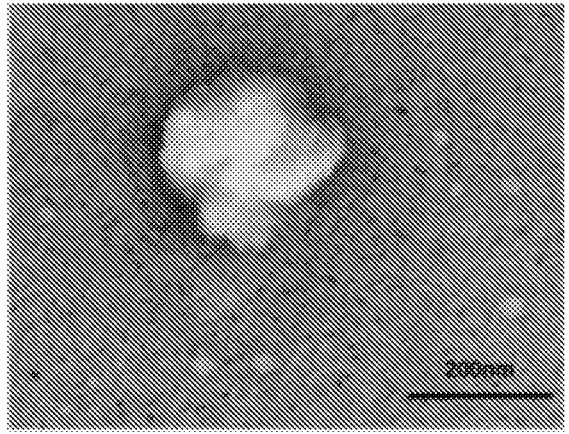
Figure 3A:
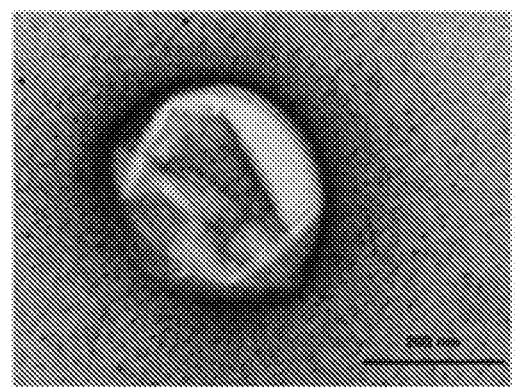
Figure 3B:
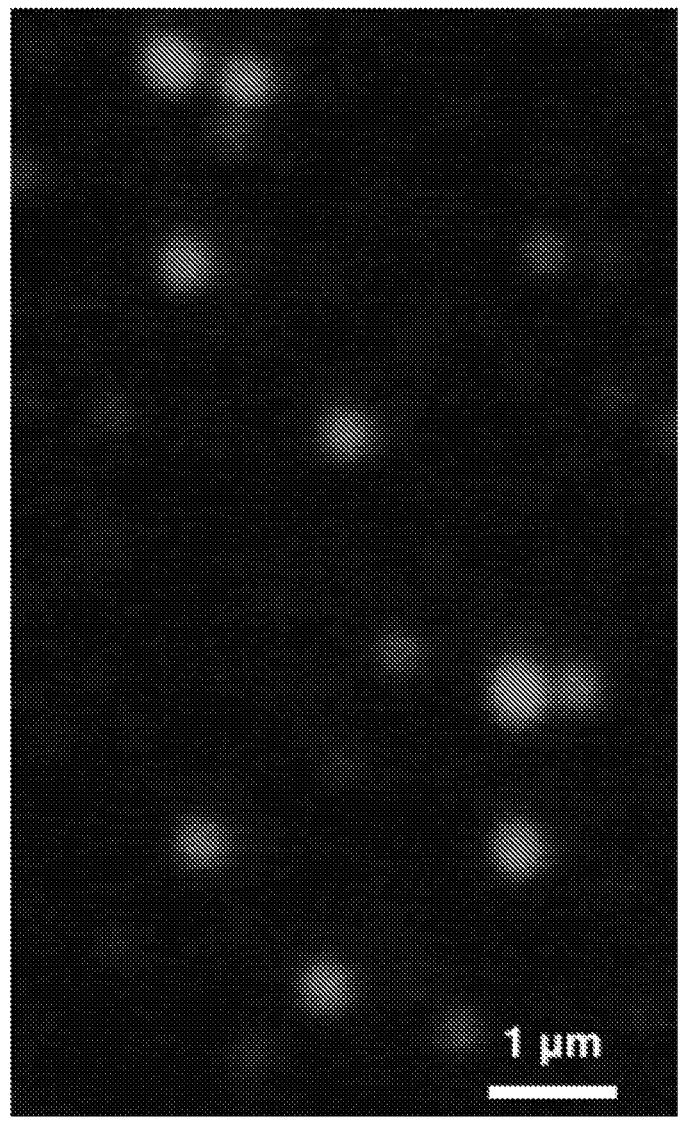
FIG. 3B shows a confocal image of the AF-ZOL DNV indicating good DNV stability.

Electrical properties of empty and loaded DNVs are shown in Table 2. AFM imaging of DNVs is shown in FIG. 2 and a TEM image of a DNV is shown in FIG. 3A and vesicle viability after storage and resuspension using confocal microscopy shows no drug leakage from the vesicle in FIG. 3B. Both DNVs and conventional liposomes were prepared using the microfluidic reactor and characterized as above.

TABLE 2

Electrical properties of empty and loaded DNVs in solution (PBS).

| Sample Name | Zeta Potential (mV) | Mobility (μmcm/Vs) | Conductance (mS/cm) |
|---|---|---|---|
| Empty Cationic DMV #1 | +19.1 | 1.261 | 17.8 |
| Empty Cationic DMV #2 | +19.3 | 1.273 | 18.5 |
| Empty Cationic DMV #3 | +20.0 | 1.319 | 19.0 |
| Loaded Cationic DMV #1 | −12.9 | −0.8529 | 17.8 |
| Loaded Cationic DMV #2 | −13.1 | −0.8644 | 18.6 |
| Loaded Cationic DMV #3 | −12.8 | −0.8471 | 19.0 |

Figure 4:
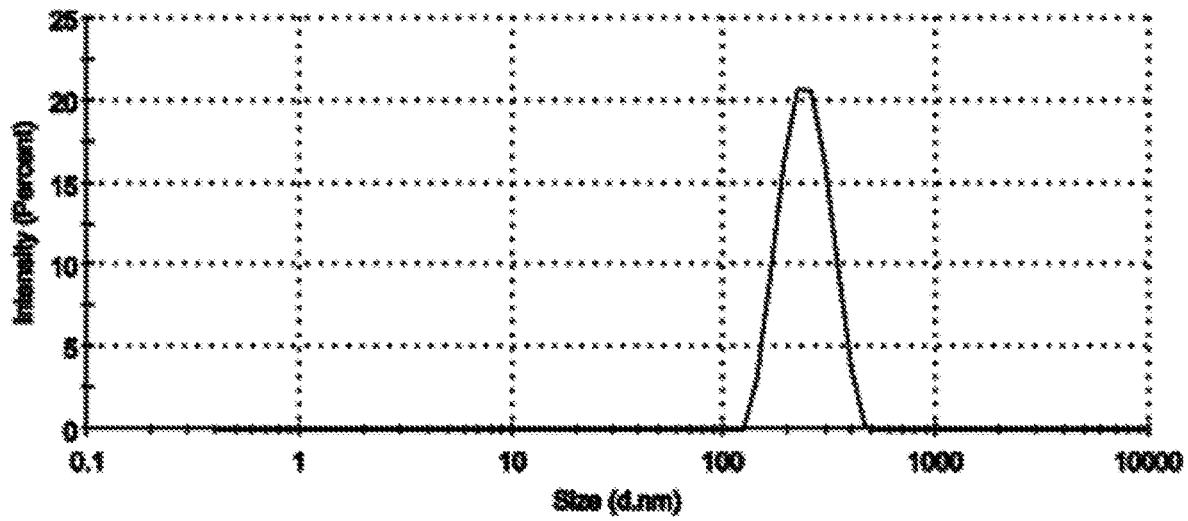
FIG. 4 illustrates population characteristics of drug loaded DNVs. Shown is a plot of size versus intensity after first lyophilization.
Figure 5A:
FIGS. 5A-5C show that AF-ZOL DNV penetrate oral mucosal barrier and deliver payload locally.
Figure 5B:
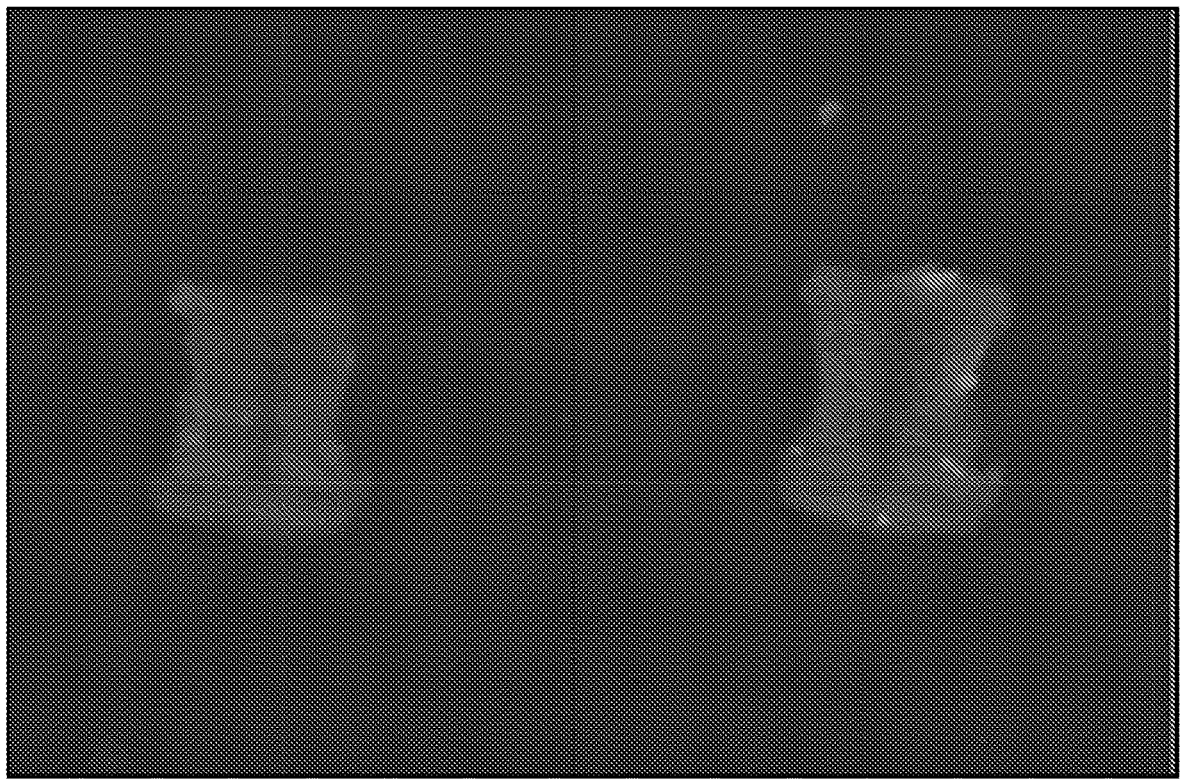
Figure 5C:
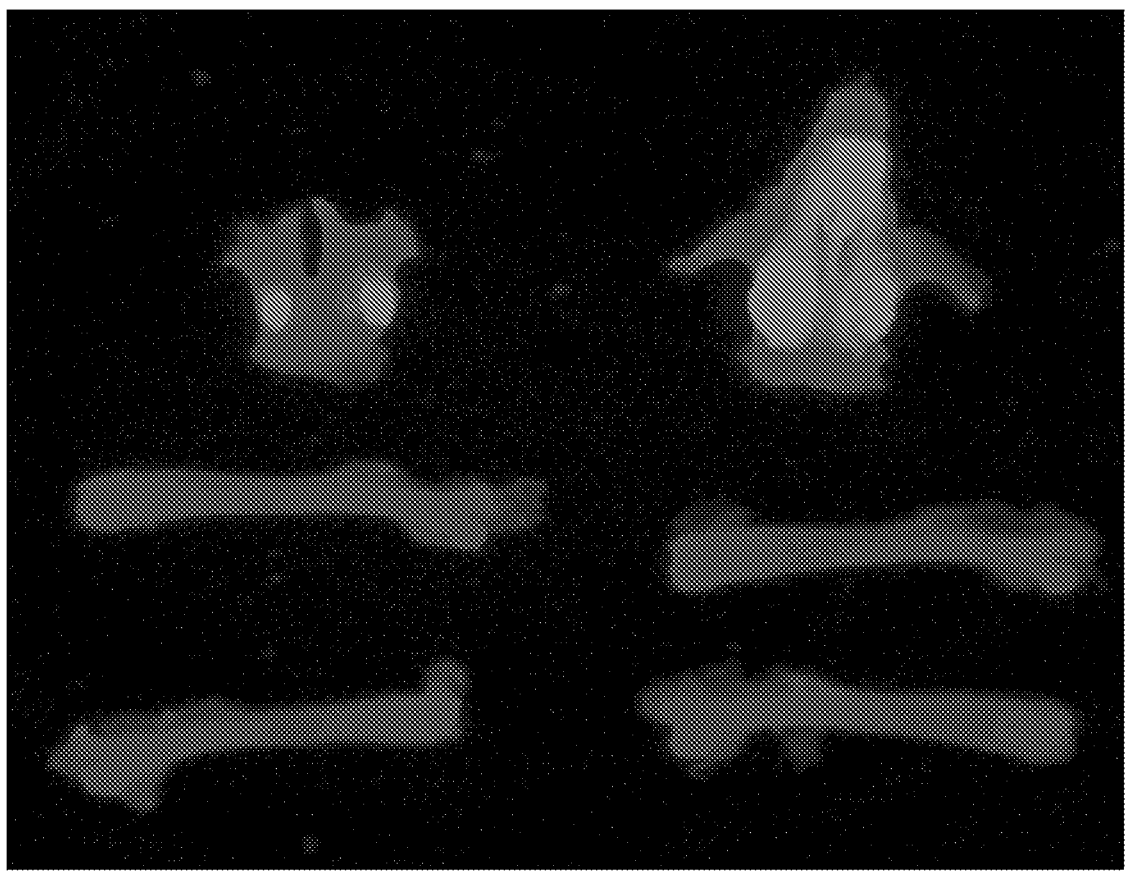
Figure 6:
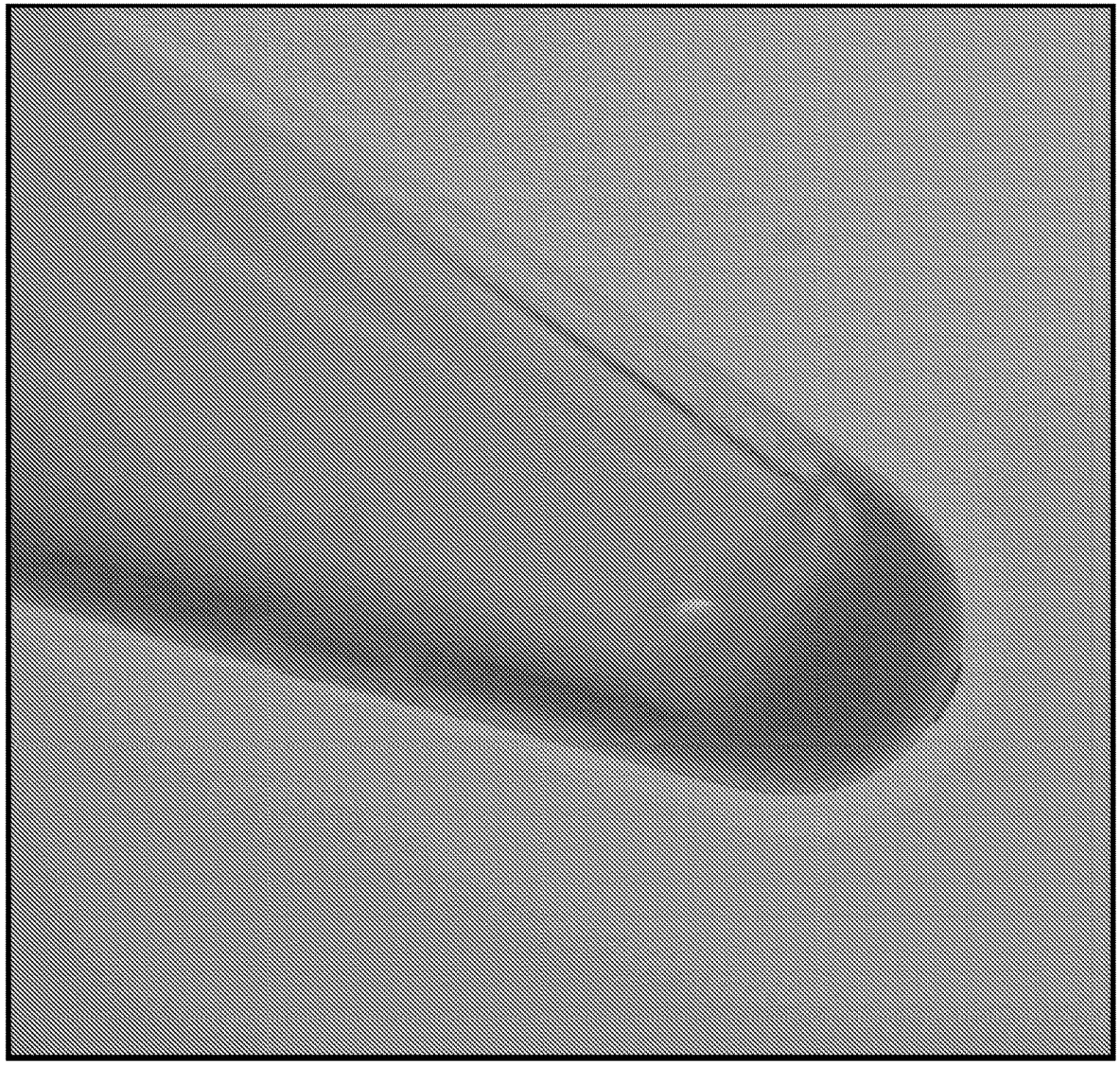
FIG. 6 shows an image of AF-ZOL loaded DNVs, macroscopic view.
Figure 7A:
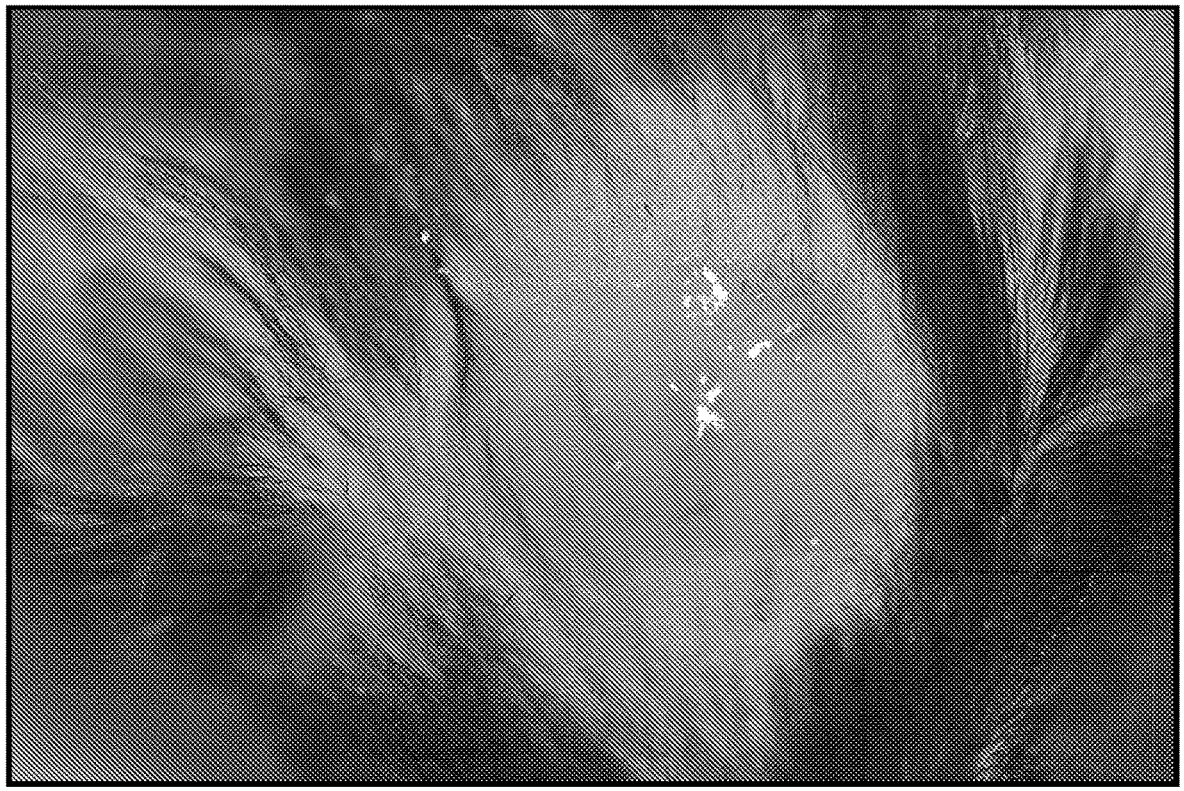
FIGS. 7A-7B show that topically applied DNVs locally deliver payload within skin layers.
Figure 7B:
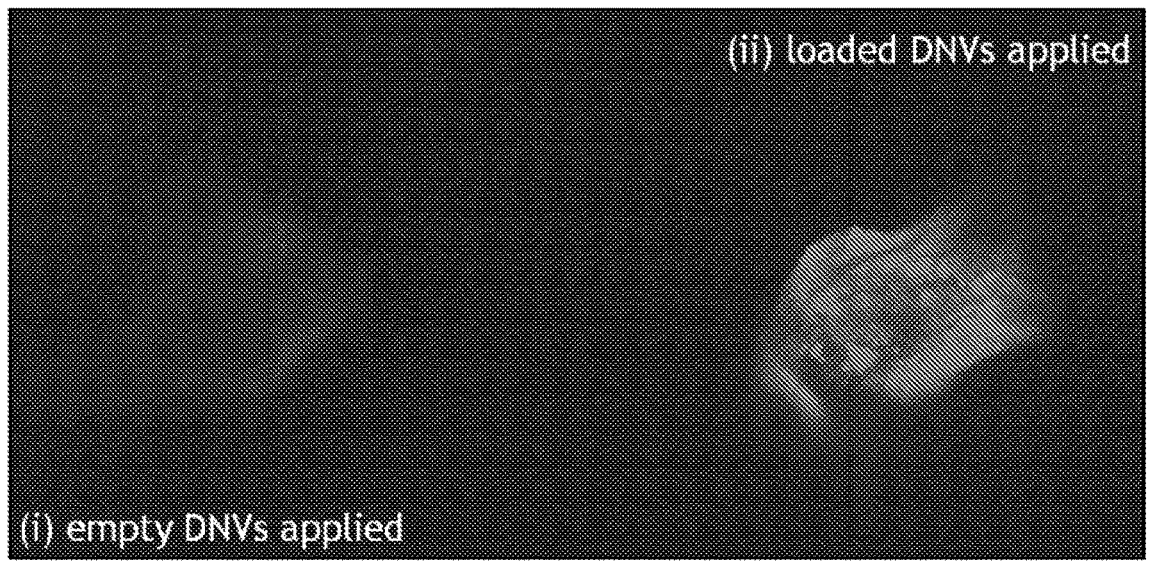
Figure 8:
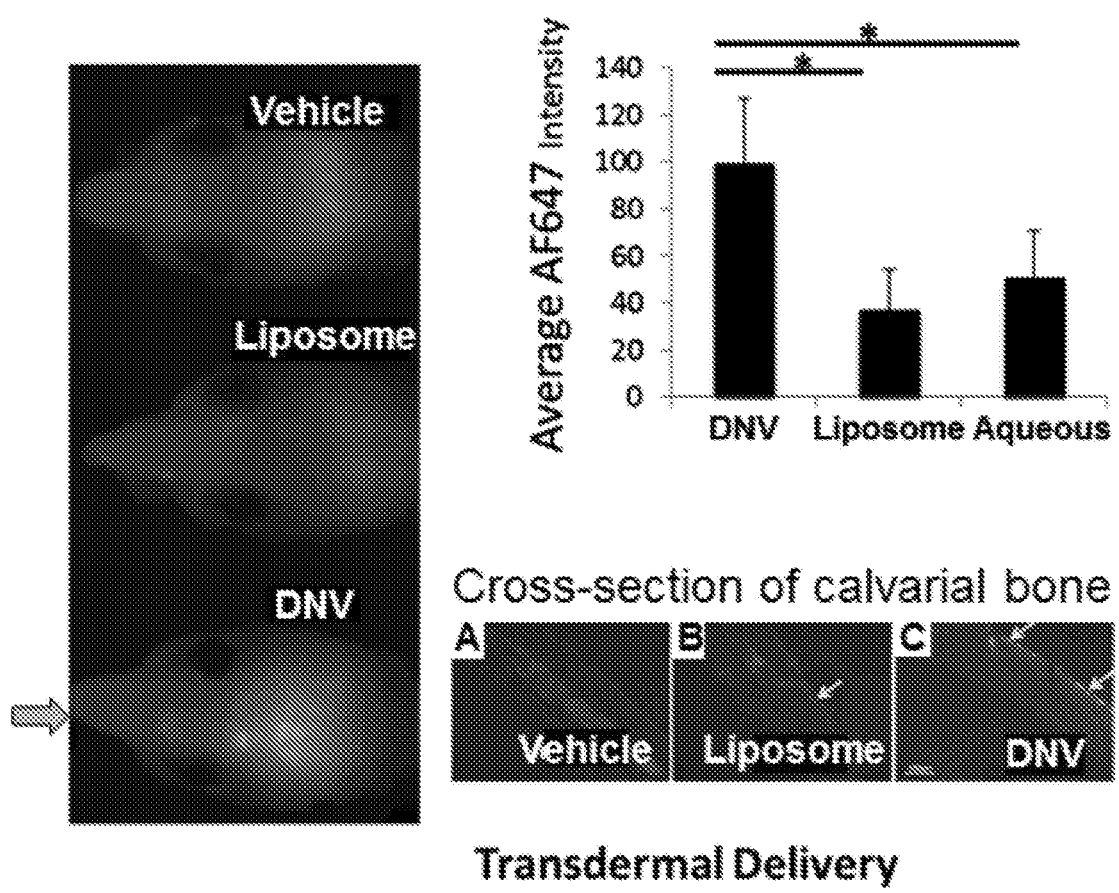
FIG. 8 illustrates significant transdermal delivery of AF-ZOL in a DNV (as compared to drug in conventional liposome or vehicle) based on fluorescence intensity of the calavarial bone, demonstrating proof-of-concept.

FIG. 4A shows the size distribution of DNVs and Table 3 shows a summary of the characterization for both DNVs and conventional liposomes

TABLE 3

Properties of microfluidic produced DNVs and liposomes encapsulating the drug AF-ZOL.

| Characteristics | Nanoparticle Type | |
|---|---|---|
| | DNV | Conventional Liposome |
| Size (diameter) | 221 ± 48 nm | 106 ± 39 nm |
| Zeta Potential | +41.7 ± 3.7 mV | +38.1 ± 1.8 mV |
| Entrapment Efficiency | 39.6% | 37.4% |

DNV stable as lyophilized powder after weeks of storage.

Example 2

In Vivo Study: DNV Application & Innovation in Trans-Oral Mucosal and Trans-Dermal Topical Application In vivo testing in mice wherein DNVs were applied to the gingival surface of the oral mucosa and to the calvarial skin showed that the DNVs were able to efficiently penetrate the oral mucosal barrier and locally deliver drug to the underlying alveolar bone, without systemic payload leakage. In the case of transdermal topical application, the DNVs delivered the payload within the layers of the skin, without penetrating through and delivering drug to the skull bone or systemically.

In particular, an in vivo study was conducted in mice (n=4) to test the performance of DNVs at the two application sites, (i) gingival surface and (ii) calvarial skin (n=2 for each.) A Negative control of empty DNVs was used, tested against the DNVs encapsulating fluorescent bone-targeting drug. Mice were sacrificed, and tissues and bone were analyzed 48 hours after application.

This study suggests that DNV deformability allows these nanovehicles to squeeze through pores significantly smaller than their diameter, while retaining their payload without rupturing. This enables them to permeate deeper through particularly obstructive barriers, such as oral mucosal membrane, and avoid potential complications by entering the target site only without systemic payload leakage (see, e.g., FIGS. 4B, 5A-5C, FIG. 6, FIGS. 7A and 7B and FIG. 8.

Discussion

A highly homogenous population of DNVs of size ~200 nm have been efficiently synthesized, to encapsulate a fluorescent bone targeting hydrophilic drug in a quick, controlled and continuous manner from a microfluidic reactor. Here, cationic DNVs were synthesized, but anionic and neutral DNVs may be similarly synthesized, with the same deformability ingredients, varying only in the incorporation of a particular charged component.

In-vivo testing in mice, specifically, application to the oral mucosa and to the calvarial skin, showed that the vehicles were able to efficiently penetrate the oral mucosal barrier and locally deliver drug to the underlying alveolar bone, without systemic payload leakage. In the case of topical application, the DNVs delivered the payload within the layers of the skin, without penetrating through and delivering drug to the skull bone or systemically.

This study suggests that their deformability allows these nano-vehicles to squeeze through pores significantly smaller than their diameter, while retaining their payload without rupturing. This enables them to permeate deeper through particularly obstructive barriers, such as oral mucosal membrane, and avoid potential complications by entering the target site without systemic payload leakage.

Impedance of DNVs in the skin, may be attributed to their size at the time of application. Though homogenous, the population was around the size of 600 nm after the second lyophilization. Studies show that nanoparticles above the size of 200 nm seem to have difficulty penetrating through to the stratum corneum (Singh et al. (2009) *AAPS J.* 11(1): 54-64; Holpuch et al. (2010) *Pharm. Res.* 27(7): 1224-1236; Šentjurc et al. (1999) *J. Control. Rel.* 59(1): 87-97). Further experimentation to determine the effect of DNV size on skin permeation is currently in progress.

Conclusion

Histological analysis permits determination of the sites of accumulation in the skin, gingiva and bone. Given their biodegradability, relatively negligible toxicity, ease of synthesis and potential for large-scale manufacturing, these DNV carriers present a novel local delivery system through the oral mucosal barrier, and locally to the skin, which may be useful for a number of dental, cosmeceutical, or regenerative purposes.

REFERENCES

1. Prausnitz, Mark R., and Robert Langer. "Transdermal Drug Delivery." Nat Biotechnol Nature Biotechnology 26.11 (2008): 1261-268.
2. Singh, H P, P Utreja, A K Tiwary, and S Jain. "Elastic Liposomal Formulation for Sustained Delivery of Colchicine: In Vitro Characterization and In Vivo Evaluation of Anti-gout Activity." The AAPS Journal AAPS J 11.1 (2009): 54-64.
3. Fleisher, D., S. M. Niemiec, C. K. Oh, Z. Hu, C. Ramachandran, and N. Weiner. "Topical Delivery of Growth Hormone Releasing Peptide Using Liposomal Systems: An in Vitro Study Using Hairless Mouse Skin." Topical Delivery of Growth Hormone Releasing Peptide Using Liposomal Systems: An in Vitro Study Using Hairless Mouse Skin. Pergamon.
4. Petelin, M., M. Šentjurc, Z. Stolič, and U. Skalerič "EPR Study of Mucoadhesive Ointments for Delivery of Liposomes into the Oral Mucosa." International Journal of Pharmaceutics 173.1-2 (1998): 193-202.
5. Madhav, N. V S., R. Semwal, D. K. Semwal, and R. B. Semwal. "Recent Trends in Oral Transmucosal Drug Delivery Systems: An Emphasis on the Soft Palatal Route." ResearchGate. Expert Opinion on Drug Delivery.
6. Patel, Viralkumar F., Fang Liu, and Marc B. Brown. "Advances in Oral Transmucosal Drug Delivery." Journal of Controlled Release 153.2 (2011): 106-116.
7. Idiart, Marco A., and Yan Levin. "Rupture of a Liposomal Vesicle." Physical Review E Phys. Rev. E 69.6 (2004).
8. Holpuch, Andrew S., Garrett J. Hummel, Meng Tong, Garrett A. Seghi, Ping Pei, Ping Ma, Russell J. Mumper, and Susan R. Mallery. "Nanoparticles for Local Drug Delivery to the Oral Mucosa: Proof of Principle Studies." Pharm Res Pharmaceutical Research 27.7 (2010): 1224-1236.
9. Šentjurc, M., K. Vrhovnik, and J. Kristl. "Liposomes as a Topical Delivery System: The Role of Size on Transport Studied by the EPR Imaging Method." Journal of Controlled Release 59.1 (1999): 87-97.
10. Huang, Yaw-Bin, Ming-Jun Tsai, Pao-Chu Wu, Yi-Hung Tsai, Yi-Hsin Wu, and Jia-You Fang. "Elastic Liposomes as Carriers for Oral Delivery and the Brain Distribution of ( )-catechin." Journal of Drug Targeting 19.8 (2011): 709-718

Example 3

Deformable Nano-Scale Vehicles for Trans-Blood Brain-Barrier Delivery

Materials

Deformable nano-scale vehicles (DNV) building blocks were purchased from Sigma Aldrich and Avanti Polar Lipids. Microfluidic system including 2 pumps, syringes, injection loop, microreactor and chip holder were purchased from Syrris. Phosphate-buffered saline (PBS), anhydrous isopropyl alcohol (IPA), chloroform and galangin (GAL) were acquired from Sigma. Dialysis membranes, 0.1 μm and 0.2 μm polyethersulfone(PES) filters, lyophilizer, rotary evaporator and centrifugation tubes were obtained from Thermo Fisher Scientific. Dynamic Light Scatterer was from Wyat, transmission electron microscope was from JEOL, atomic force microscope was from Bruker and mass spectrometer was from Advion.

Methods

Figure 9:
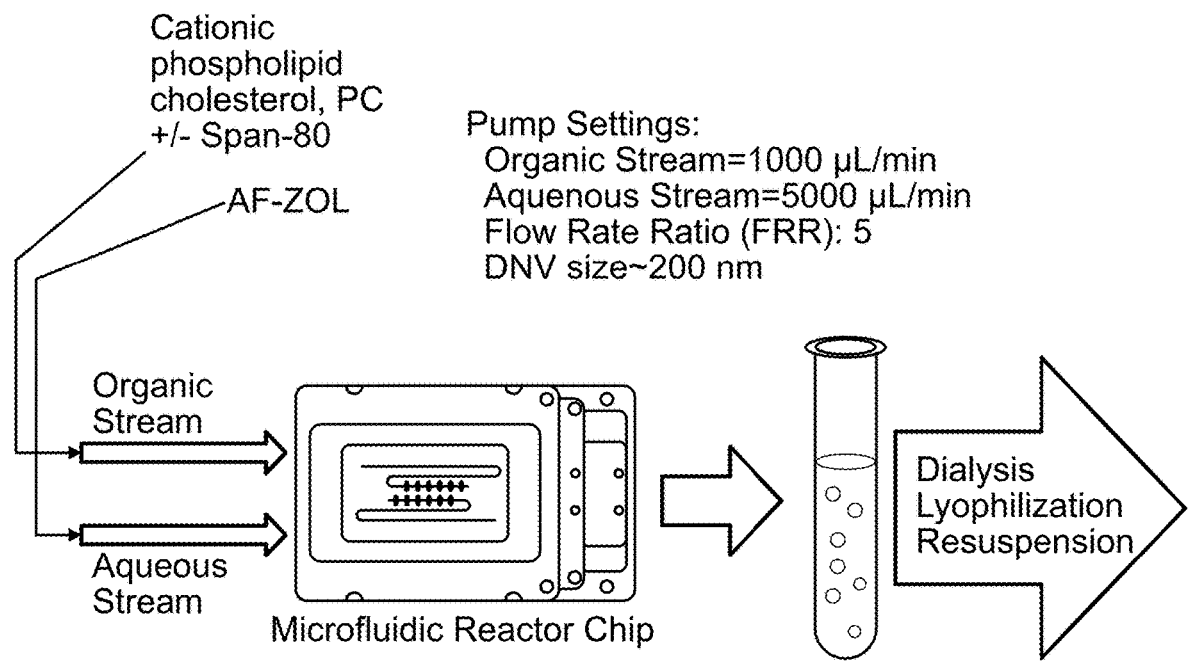
FIG. 9 illustrates a microfluidic synthesis scheme for preparation of the hydrophobic drug galangin a bioflavonoid with low brain permeability.
Figure 9:
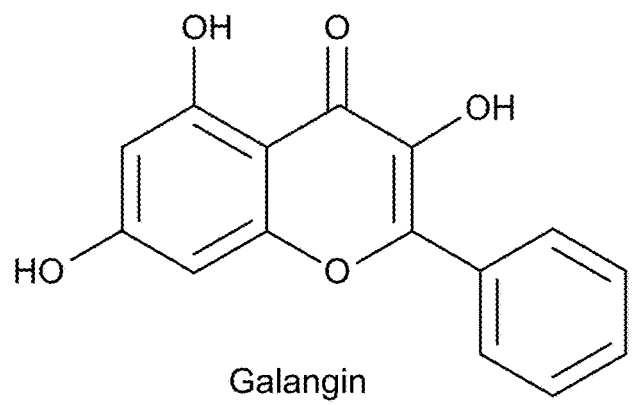

In various embodiments DNV building blocks are composed of lipids anionic phospholipids, cholesterol, and a non-ionic detergent Span 80. The exact lipid components, detergent and molar ratio used are determined based on the intended application of the DNVs as shown in the scheme in FIG. 9. In illustrative, but non-limiting embodiments, 1,2-Dipalmitoyl-sn-glycero-3-phosphocholine (DPPC), cholesterol and dihexadecyl phosphate (DHP) are dissolved in chloroform and mixed in a molar ratio of 4:4:2; then chloroform was allowed to evaporate overnight or in the rotary evaporator. The lipid mixture was dissolved IPA to get a concentration of 20 mM. Then 1.5% (w/w of the lipid mix) of Tween 20 or Span 80 was added to the lipid mixture and mix. Ten millimolar galangin (GAL) is dissolved in IPA, was added to the lipid/detergent mixture in a 4:1 molar ratio followed by filtration through 0.2 µm PES filter. PBS and distillate (dd) water are filtered using the 0.1 µm PES filter. The flow rate ratio of 3-4 (PBS or dd water to IPA) was set up in the pumps and the system was washed with IPA and either PBS or distillate water. Typically the 26 µL microreactor but larger sizes of the reactor can be used to optimize size and morphology can be used for the synthesis of the DNV. Once the microfluidic system has been washed the lipid/GAL/detergent mixture is loaded in the injection loop, then pumped through the micreactor together with and aqueous solution (PBS or dd water) using a second pump at 25-40° C. and 1 bar pressure to produce the GAL encapsulated DNV (Lipo-GAL). After the DNVs are syntheses they are concentrated either by dialysis and lyophilization or ultra centrifugation to produce a pellet of the DNV. Size characterization was then done by DLS and size distribution shown in FIG. 10. The GAL that was not incorporate in the liposomes is removed from the solution using ultracentrifugation or dialysis.

Characterization

Figure 10:
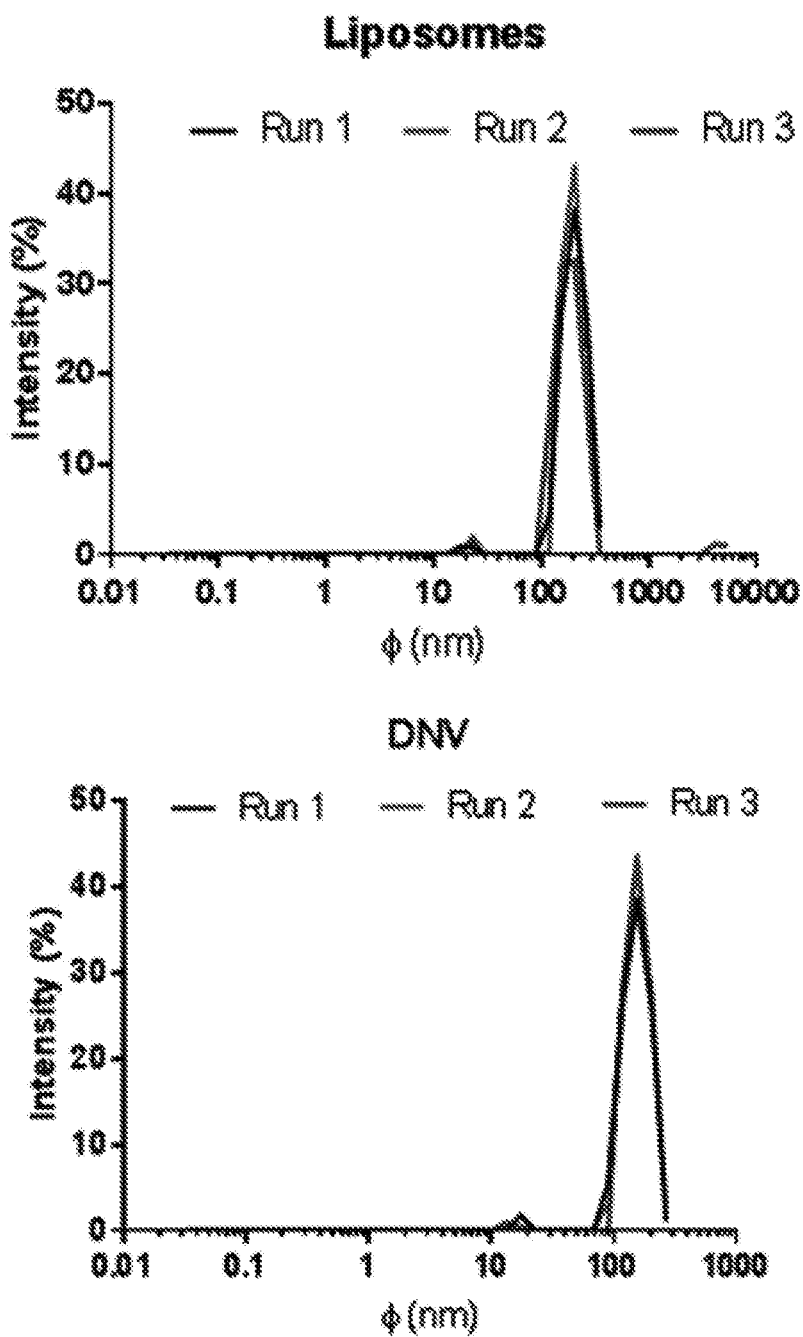
FIG. 10 illustrates the DLS analysis of the microfluidic produced Lipo-GAL DNV showing a size roughly of 150 nm.

The size of the Lipo-Gal DNV was determined by Dynamic Light Scattering in a Wyatt instrument (FIG. 10). This measurement is confirm by transmission electron microscope and atomic force microscope. The entrapment efficiency is calculated by calculating the free GAL using HPLC and mass spectroscopy.

Discussion.

Deformable nano-scale vehicles are elastic nanoparticles that, in certain embodiments, are composed of phospholipids, such as 1,2-Dipalmitoyl-sn-glycero-3-phosphocholine (DPPC), N-(2,3-Dioleoyloxy-1-propyl) trimethylammonium (DOTAP), 1,2-Dioleoyl-sn-glycero-3-phosphoethanolamine (DOPE). Apart from phospholipids, DNVs contain two key ingredients: cholesterol, a membrane regulator and a non-ionic detergent (e.g., Span 80, Tween 20, etc.) that acts as an edge activator, adding deformability to the lipid bilayer of the nanoparticle.

In one illustrative, but non-limiting embodiment, the lipids (including cholesterol) and the edge activator are present in an 85:15 w/w ratio.

The exact molar ratio and types of lipid components used are determined based on the intended application of the DNVs. For example, in one illustrative embodiment for trans-oral mucosal and topical application, a 5:3:2 molar ratio (DPPC:Cholesterol:DOTAP) can be used, with the mixture containing 15% Span 80 by weight.

These components, dissolved in an organic solvent such as isopropyl alcohol (IPA) are combined with aqueous solution (PBS or DI water) via separate inputs into a microfluidic reactor system for efficient and continuous synthesis at 25° C.-40° C. and 1 bar pressure. The microfluidic reactor channels provide high shear stress and controlled mixing, with minimized turbulence, resulting in well-defined DNV populations, and eliminating the need for post-processing, such as sonication or extrusion to obtain appropriate size. Upon transitioning from organic to aqueous phase, the components described self-configure into DNVs, according to their thermodynamic stability in aqueous solvent.

The DNVs are non-toxic, prepared highly reproducibly with little batch to batch variability, scalable, very homogenous in population and distribution, of tunable size, and provide highly localized payload delivery. Our research shows that this method can produce homogenous populations of size 50 nm to sizes in the micron range. Resultant DNV size is tuned primarily by the adjustment of the flow rate ratio (FRR) between the aqueous phase and the organic, lipid containing, phase. Our investigations have shown that increasing the flow rate ratio directly decreases resultant DNV size as well as reducing size dispersity. For trans-oral mucosal and topical application, a FRR of 100 was used, to obtain DNVs of size centered at 250 nm from the aforementioned components. Note that the same FRR may produce different sized DNVs, depending on the particular types of components used.

The DNVs can be synthesized to encapsulate various classes of drugs, including, for example, small molecules, proteins, RNA, and DNA. They can efficiently encapsulate both hydrophilic and hydrophobic drugs, though are more successful with the latter. In our research, we have synthesized them to successfully encapsulate the following hydrophilic drugs: Fluorescein derivative, Fluorescein Isothiocyanate (FITC), and a fluorescently tagged bone targeting drug. In the case of hydrophobic drugs, we actively use DNVs to encapsulate Galangin, to be delivered through the blood brain barrier. The solubility of a given drug dictates the phase (organic or aqueous) that it is introduced in to the microfluidic reactor, with highest encapsulation when both drug and DNV components are in the same (organic) phase.

Another interesting tunable feature is charge contained on a DNV: DNVs of various charge concentrations (zeta potentials) can be created, through the use of different combinations of charged phospholipid components. We have synthesized neutral (DPPC, cholesterol, DOPE), cationic (DPPC,cholesterol, DOTAP) and anionic (DPPC,cholesterol,DHP) DNVs. The strength of charge can be tuned by adjusting the concentration of a particular charged component in the DNV preparation mixture.

Prototype preparation for in-vivo use (trans-oral mucosal and topical application):

DNV samples collected from the microfluidic reactor are twice dialyzed overnight through a 20K membrane to remove 99.9% of free drug from solution. Following dialysis, samples are lyophilized to a powder and resuspended in a final volume of 10 µL, appropriate for topical and gingival application, via direct pipette application on anesthetized mice. Intended final clinical use in this domain is likely to be in the form of a pre-filled syringe.

DNV application & innovation in trans-oral mucosal and topical application: In-vivo testing in mice, specifically, application to the gingival surface of the oral mucosa and to the calvarial skin, showed that the vehicles were able to efficiently penetrate the oral mucosal barrier and locally deliver drug to the underlying alveolar bone, without systemic payload leakage. In the case of topical application, the DNVs delivered the payload within the layers of the skin, without penetrating through and delivering drug to the skull bone or systemically.

This study suggests that the deformability of DNVs allows these nano-vehicles to squeeze through pores significantly smaller than their diameter, while retaining their payload without rupturing. This enables them to permeate deeper through particularly obstructive barriers, such as oral mucosal membrane, and avoid potential complications by entering the target site without systemic payload leakage.

Materials (Including Characterization)

Microfluidic reactor system, 26 μL reactor chip but larger sizes could be used as needed to control size and morphology, DI Water, PBS, isopropyl alcohol, chloroform, dialysis membranes, lyophilizer, DNV building blocks, including membrane components, membrane regulator and, deformability ingredients. Zetasizer (Malvern Z series), Dynamic Light Scatterer (Wyatt). Transmission Electron Microscope (JEOL). Atomic Force Microscope (Bruker)

In our research, various synthesized DNV populations have been characterized in terms of size, zeta potential, entrapment efficiency, qualitative elasticity, and morphology.

Furthermore, these DNVs remain stable in aqueous suspension for extended periods of time, remaining viable even after two months, though there is some reduction in population homogeneity, likely due to fusion event.

Characterization of the blood brain-barrier permeability of the DNV was measured using a Caco-2 cell system and further confirmed by conducting pharmacokinetic studies in mice.

Example 4

Use of DNVs to Generate Stable CNS-Targeted Liposomes Capable of Penetrating the Blood-Brain Barrier (BBB)

The Tf-Lipo-Gal DNV can be prepared as described in Example 3 in the microfluidic reactor by including a DDPE (18:1 dodecanyl PE, or 1,2-dioleoyl-sn-glycero-3-phosphoethanolamine-N-(dodecanyl)) conjugated Transferrin (Tf) protein in the organic phase. The DNV isolation is as above using ultracentrifugation.

Synthesis of Tf-DDPE Conjugate

Figure 11:
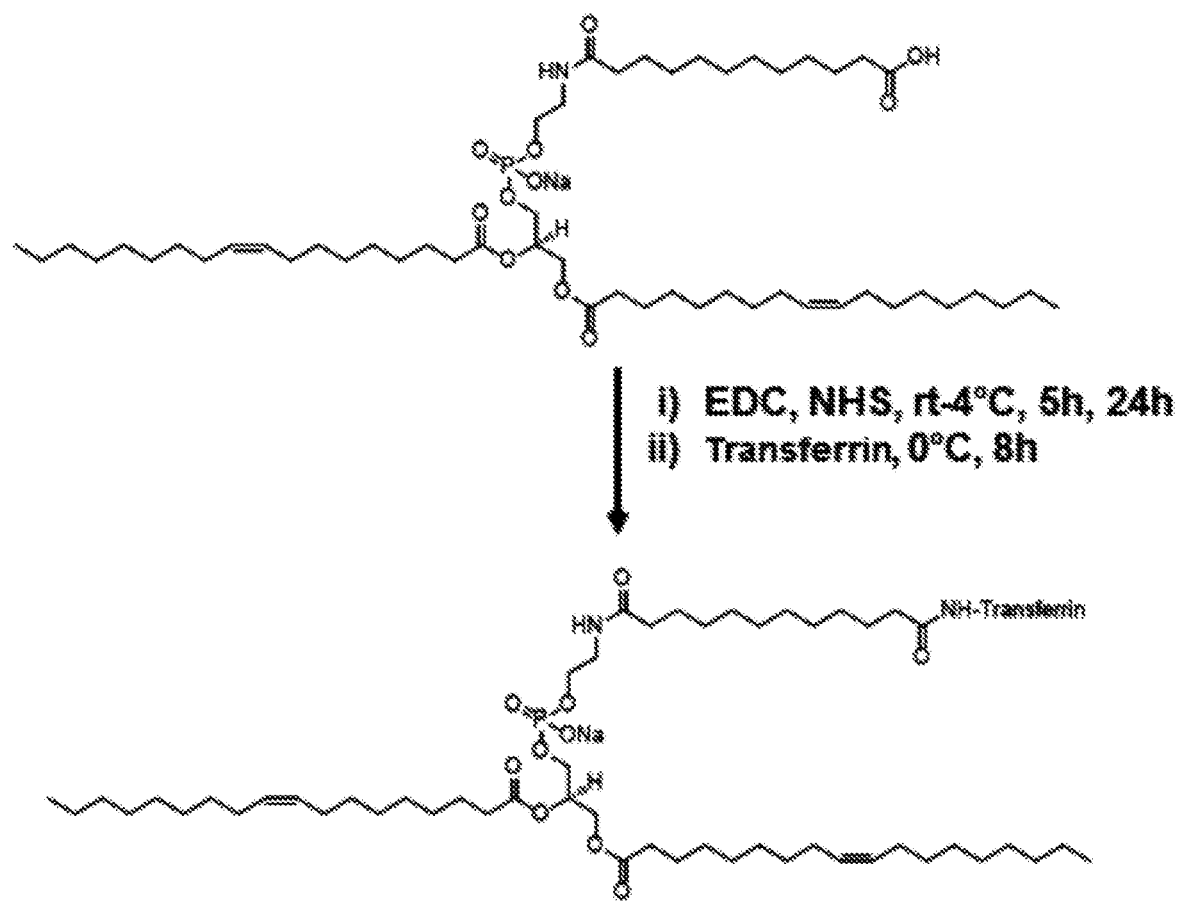
FIG. 11 illustrates the synthesis of a transferin conjugated phospholipid (Tf-DPPE).
Figure 12:
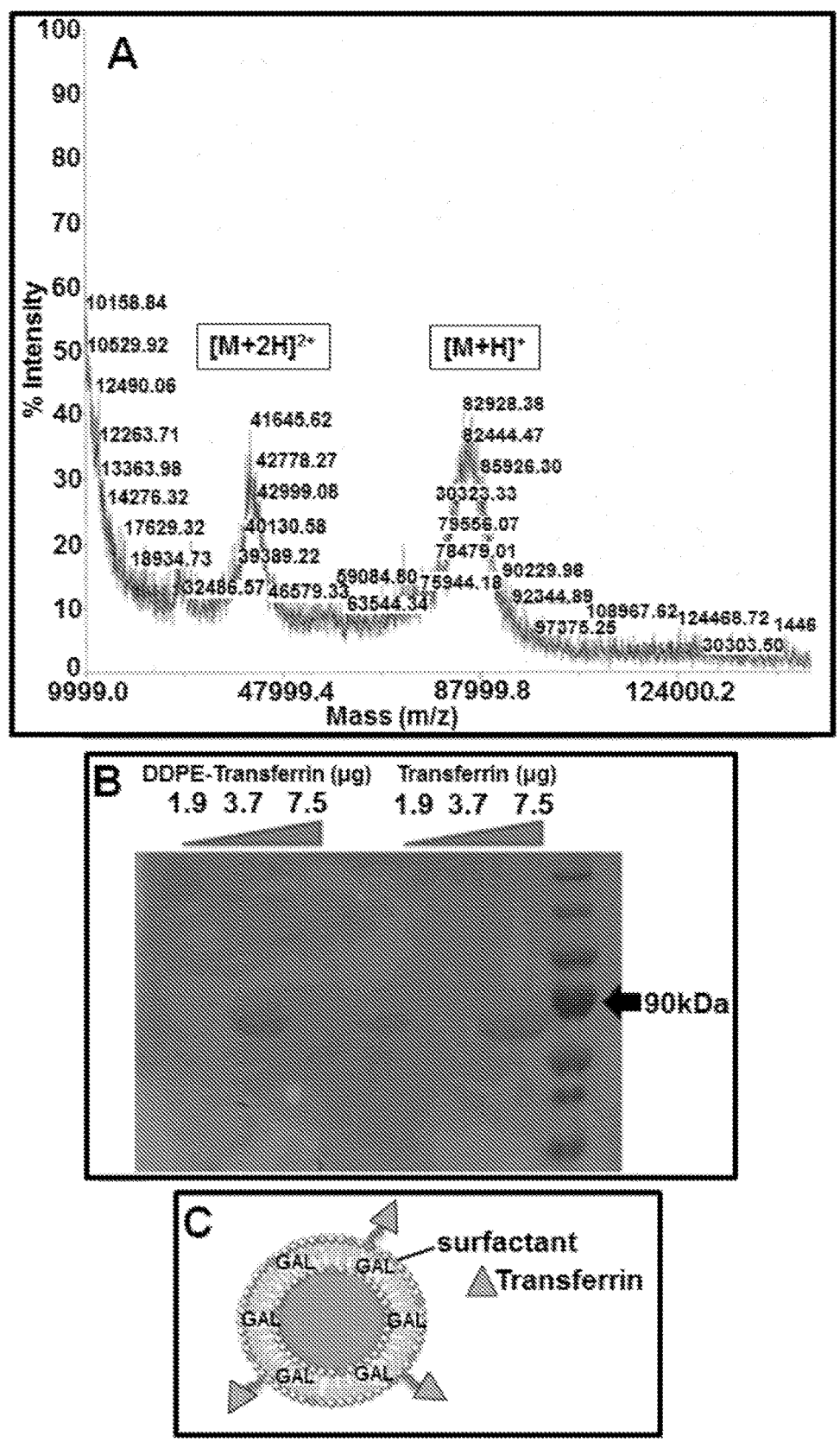
FIG. 12, panels A-C, illustrates A) MALDI-TOF spectrogram of DDPE-Transferrin conjugate (B) SDS PAGE of the Tf-DDPE and Transferrin (C) Representative cartoon of the Tf-Lipo-Gal.

Transferrin was conjugated to DDPE by utilizing carbodiimide chemistry in PBS (Muthu et al., 2015). In general, for conjugation of transferrin to DDPE, N-hydroxy-succinimide (NETS) and 1-ethyl-3-(3-dimethylaminopropyl) carbodiimide hydrochloride (EDC.HCl) were added to a solution of DDPE in PBS (pH 5.8) with a molar ratio of 1:5:5 (DDPE:EDC.HCl:NHS). Specifically, to a stirred solution of DDPE (50 mg, 0.05 mmol) in 1.5 mL PBS (pH 5.8) was added EDC.HCl (49 mg, 0.26 mmol) and NETS (30 mg, 0.26 mmol). The reaction mixture was stirred at 25° C. for 5 h, followed by stirring at 4° C. for 24 h. Crude mixture was further mixed with 1 mL of 2% (w/v) transferrin and stirred at 4° C. for 8 h. Reaction mixture was further divided in to two aliquots and were dialyzed by 3 mL dialyzing cassettes (MW cutoff: 20 kDa) against distilled water (ddH2O) for 48 h—with frequently changing ddH2O after first 2 h, and repeated thrice after each 12 h—in order to remove excess DDPE, NETS and EDC hydrochloride. The solution obtained was flash frozen and lyophilized to afford DDPE-Transferrin conjugate as colorless powder in good yield, which was stored at −20° C. under inert atmosphere until required for liposome synthesis (FIG. 11). MALDI-TOF characterization is shown in FIG. 12 along with SDS-PAGE and representative cartoon for Tf-Lipo-Gal. The MALDI mass spectroscopic analysis shows that the DDPE to transferrin ratio is (4:1).

Example 5

Use of DNVs to Generate Stable CNS-Targeted Liposomes Capable of Penetrating the Bloodbrain Barrier (BBB) such as for Treatment of Glioblastoma Multiformed (GBM)

DNVs may be used to deliver potential therapeutic agents for the treatment of glioblastoma multiforme (GBM), the most aggressive and lethal of all cancers. GBM is refractory to conventional treatment due, in part, to the invasive nature of GBM cells and sequestration of these tumors to the central nervous system (CNS).

As GBM may arise from lower grade gliomas and more than 70% of these have isocitrate dehydrogenase IDH1/2 mutations leading to gain-of-function increases in enzymatic activity, there is interest in IDH1 inhibitors as therapeutics. We are encapsulating commercially available IDH1 inhibitors such as AGI-5198 in DNVs to test efficacy in a variety of glioma cell lines and in vivo models of glioma and GBM.

In addition, as recent studies have shown that mutated tumor-suppressor p53—found in >50% of human tumors— produces aggregation-prone peptides resulting in loss-of-function, we are also encapsulating interrupters of p53 aggregation. Delivery of these peptidic interrupters in the DNVs would enable in vivo evaluation of any anti-tumor effects.

Example 6

Use of DNVs for Delivery of Large Biomolecules Across the BBB for AD sAPPalpha is a 100 Kd fragment from alpha processing of APP and has recently been shown by the Drug Discovery Lab to inhibit beta secretase BACE1. As BACE inhibitors have potential as Alzheimer's Disease (AD) therapeutics, delivery of sAPPalpha across the BBB would enable its evaluation as a potential BACE inhibitor. We are generating DNVs to stably encapsulate recombinantly produced sAPPalpha and will evaluate their efficacy in AD mouse models.

Example 7

Use of DNVs for Delivery of miRNA Across the BBB to the Brain for AD

DNVs can also be used for delivery of micro RNAs (miRNA) such as miRNA-107 (miR-107) in for Alzheimer's disease (AD) treatment. miRNAs are endogenously expressed forms of small interfering RNA (siRNA) that are non-protein coding RNAs which function as regulators of gene expression. miR-107 has been shown to be decreased in cerebral spinal fluid (CSF) in early AD and this decrease may accelerate disease progression through upregulation of BACE expression and activity. Thus increasing the levels of miR-107 in the brain could potentially normalize BACE expression and activity, reduce Aβ peptide production (implicated in AD pathology), increase sAPPalpha and be a potential therapeutic approach for AD. Delivery of miR-107 in CNS-targeted DNVs prepared in our microfluidic reactor affords the possibility of modulating BACE in vivo. We plan to test these DNVs in AD mice both for BBB permeability and efficacy. Similarly other miRNAs that modulate disease pathology in AD and other CNS disorders can be synthesized and tested in vivo.

Example 8

Use of DNVs for Delivery of Drugs Across the BBB to the Brain by the Transdermal Application for Parkinson's Disease (PD)

DNVs can be used to encapsulate and deliver PD drug pramipexole transdermally to ease delivery and increase compliance. Pramipexole is a low molecular weight therapeutic with good water solubility that stimulates dopamine receptors in the brain. Due to its highly polar hydrophilic nature (log P of 0.4 measured experimentally), transdermal delivery of the free drug across the stratum corneum (outer layer of skin) is difficult. We are encapsulating pramipexole in DNVs to test the ability of these DNV nanoparticles to cross the stratum corneum and allow transdermal delivery of pramipexole to the brain.

Example 9

Use of DNVs for Delivery of Sirtuin 1 (SirT1) Enhancers for Amyotrophic Lateral Sclerosis (ALS)

DNVs can also be used to encapsulate sirtuin 1 (SirT1) enhancers for ALS therapy. In vivo studies in mouse models of ALS have shown that increasing SirT1 levels ameliorates the ALS phenotype. Molecules that increase SirT1 levels will be encapsulated in DNVs for transdermal delivery for the treatment of ALS and will tested in mouse models of ALS.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A deformable nanoscale drug delivery vehicle (DNV) for the delivery of a therapeutic agent to the brain of a mammal, said vehicle consisting of:
a liposome consisting of a lipid bilayer disposed around an aqueous compartment and a therapeutic agent disposed inside said compartment wherein:
said lipid bilayer consists of either at least two phospholipids or at least one phospholipid in combination with N-(2,3-Dioleoyloxy-1-propyl) trimethylammonium (DOTAP), cholesterol, and a non-ionic detergent, and where the w/w ratio of lipids, including cholesterol, to non-ionic detergent ranges from about 85:5 to about 85:20, and the ratio of total phospholipid to cholesterol ranges from about 12:2 to about 5:4, and where said liposome ranges from about 60 nm to about 150 nm average diameter;
said therapeutic agent is usable for treatment of a neurological disorder; and
said liposome is effective to retain said therapeutic agent when in circulation in the blood circulation and is capable of deforming sufficiently to pass through pores comprising the blood brain barrier of a mammal while retaining said therapeutic agent.

2. The nanoscale drug delivery vehicle of claim 1, wherein said at least two phospholipids are independently selected from the group consisting of 1,2-Dipalmitoyl-sn-glycero-3-phosphocholine (DPPC), dihexadecyl phosphate (DHP), and 1,2-Dioleoyl-sn-glycero-3-phosphoethanolamine (DOPE), or wherein the at least one phospholipid combined with DOTAP is selected from the group consisting of DPPC, DHP, and DOPE.

3. The nanoscale drug delivery vehicle of claim 1, wherein the nanoscale drug delivery vehicle has at least two phospholipids, and said at least two phospholipids comprise DPPC and a second phospholipid.

4. The nanoscale drug delivery vehicle of claim 3, wherein the ratio of DPPC to said second phospholipid ranges from 2:1 to 1:2.

5. The nanoscale drug delivery vehicle of claim 1, wherein the ratio of the total of combination of all of the phospholipids and the DOTAP to cholesterol ranges from about 10:2 to about 6:2.

6. The nanoscale drug delivery vehicle of claim 1, wherein said non-ionic detergent is selected from the group consisting of sorbitan monooleate, polysorbate 20, stearyl poly (10) oxy ethylene ether, stearyl poly (20) oxyethylene ether, oleyl poly (10) oxy ethylene ether, and stearyl poly (21) oxyethylene ether.

7. The nanoscale drug delivery vehicle of claim 6, wherein said non-ionic detergent is sorbitan monooleate and is present in an amount of about 10% to about 20% by weight.

8. The nanoscale drug delivery vehicle of claim 1, wherein said nanoscale drug delivery vehicle is neutrally charged.

9. The nanoscale drug delivery vehicle of claim 8, wherein the nanoscale drug delivery vehicle has at least two phospholipids, and said at least two phospholipids comprise DPPC and DOPE.

10. The nanoscale drug delivery vehicle of claim 1, wherein said nanoscale drug delivery vehicle is cationic.

11. The nanoscale drug delivery vehicle of claim 10, wherein the nanoscale drug delivery vehicle has at least one phospholipid in combination with DOTAP, and said at least one phospholipid comprises DPPC.

12. The nanoscale drug delivery vehicle of claim 1, wherein said nanoscale drug delivery vehicle is anionic.

13. The nanoscale drug delivery vehicle of claim 12, wherein the nanoscale drug delivery vehicle has at least two phospholipids, and said at least two phospholipids comprise DPPC and DHP.

14. The nanoscale drug delivery vehicle of claim 1, wherein said nanoscale drug delivery vehicle contains a cytotoxic and/or cytostatic agent.

15. The nanoscale drug delivery vehicle of claim 1, wherein said liposome is able to cross the blood brain barrier in a mammal when administered to said mammal via intravenous administration.

16. A pharmaceutical formulation comprising a deformable nanoscale drug delivery vehicle (DNV) of claim 1 and a pharmaceutically acceptable carrier.

17. A method of delivering a therapeutic agent to the brain of a subject, said method comprising administering to said subject the deformable nanoscale drug delivery vehicle of claim 1, wherein said drug delivery vehicle crosses the blood brain barrier of said subject and thereby delivers said therapeutic agent to the brain of said subject.

\* \* \* \* \*